(12) United States Patent
Chun et al.

(10) Patent No.: US 11,751,473 B2
(45) Date of Patent: Sep. 5, 2023

(54) ORGANIC LIGHT EMITTING ELEMENT

(71) Applicant: LG CHEM, LTD., Seoul (KR)

(72) Inventors: Minseung Chun, Daejeon (KR); Sang Young Jeon, Daejeon (KR); Tae Yoon Park, Daejeon (KR); Seongmi Cho, Daejeon (KR)

(73) Assignee: LG CHEM, LTD., Seoul (KR)

( * ) Notice: Subject to any disclaimer, the term of this patent is extended or adjusted under 35 U.S.C. 154(b) by 620 days.

(21) Appl. No.: 16/069,123

(22) PCT Filed: Jul. 5, 2017

(86) PCT No.: PCT/KR2017/007147
§ 371 (c)(1),
(2) Date: Jul. 10, 2018

(87) PCT Pub. No.: WO2018/021714
PCT Pub. Date: Feb. 1, 2018

(65) Prior Publication Data
US 2019/0006602 A1    Jan. 3, 2019

(30) Foreign Application Priority Data

Jul. 26, 2016  (KR) .................. 10-2016-0094936

(51) Int. Cl.
*H10K 85/60* (2023.01)
*C07D 487/04* (2006.01)
(Continued)

(52) U.S. Cl.
CPC ........ *H10K 85/6572* (2023.02); *C07C 211/61* (2013.01); *C07D 209/86* (2013.01); *C07D 307/91* (2013.01); *C07D 403/10* (2013.01); *C07D 403/12* (2013.01); *C07D 403/14* (2013.01); *C07D 405/14* (2013.01);
(Continued)

(58) Field of Classification Search
CPC ...... H01L 2251/5384; H01L 2251/552; H10K 2101/30; H10K 2101/90
See application file for complete search history.

(56) References Cited

U.S. PATENT DOCUMENTS

2011/0279020 A1    11/2011  Inoue et al.
2012/0205632 A1    8/2012   Shitagaki et al.
(Continued)

FOREIGN PATENT DOCUMENTS

CN    102439004 A    5/2012
CN    103081155 A    5/2013
(Continued)

*Primary Examiner* — Sean M DeGuire
(74) *Attorney, Agent, or Firm* — Bryan Cave Leighton Paisner LLP

(57) ABSTRACT

The present specification relates to an organic light emitting device including: an anode; a cathode disposed to face the anode; and a light emitting layer disposed between the anode and the cathode, in which the light emitting layer includes: a host including a P-type host and an N-type host, which produce an exciplex; and a phosphorescent dopant, and the host including the P-type host and the N-type host, which produce an exciplex, emits a photoluminescence light with a longer wavelength than a wavelength of each of the P-type host and the N-type host.

8 Claims, 5 Drawing Sheets

(51) Int. Cl.
*C07D 209/86* (2006.01)
*C07D 487/14* (2006.01)
*C07D 471/06* (2006.01)
*C07D 403/10* (2006.01)
*C07D 403/14* (2006.01)
*C07D 405/14* (2006.01)
*C07D 403/12* (2006.01)
*C09K 11/06* (2006.01)
*C07C 211/61* (2006.01)
*C07D 307/91* (2006.01)
*C07D 471/10* (2006.01)
*C07D 487/16* (2006.01)
*C07D 498/06* (2006.01)
*H10K 50/11* (2023.01)
*H10K 101/10* (2023.01)
*H10K 101/30* (2023.01)
*H10K 101/00* (2023.01)

(52) U.S. Cl.
CPC ......... *C07D 471/06* (2013.01); *C07D 471/10* (2013.01); *C07D 487/04* (2013.01); *C07D 487/14* (2013.01); *C07D 487/16* (2013.01); *C07D 498/06* (2013.01); *C09K 11/06* (2013.01); *H10K 85/615* (2023.02); *H10K 85/622* (2023.02); *H10K 85/626* (2023.02); *H10K 85/633* (2023.02); *H10K 85/636* (2023.02); *H10K 85/654* (2023.02); *H10K 85/657* (2023.02); *C07C 2603/18* (2017.05); *C07C 2603/42* (2017.05); *C07C 2603/97* (2017.05); *C09K 2211/1018* (2013.01); *H10K 50/11* (2023.02); *H10K 85/624* (2023.02); *H10K 85/6574* (2023.02); *H10K 2101/10* (2023.02); *H10K 2101/30* (2023.02); *H10K 2101/90* (2023.02)

(56) References Cited

U.S. PATENT DOCUMENTS

| | | |
|---|---|---|
| 2013/0240933 A1 | 9/2013 | Yamazaki et al. |
| 2013/0320368 A1 | 12/2013 | Seo et al. |
| 2014/0084274 A1 | 3/2014 | Yamazaki et al. |
| 2015/0318478 A1* | 11/2015 | Pflumm ................ C09B 15/00 544/212 |
| 2016/0072078 A1* | 3/2016 | Lee ..................... H01L 51/0071 257/40 |
| 2017/0117488 A1 | 4/2017 | Ahn et al. |
| 2017/0125699 A1 | 5/2017 | Ahn et al. |
| 2017/0186965 A1 | 6/2017 | Parham et al. |
| 2017/0207399 A1 | 7/2017 | Parham et al. |
| 2018/0037546 A1* | 2/2018 | Sugino ................ C07D 409/14 |

FOREIGN PATENT DOCUMENTS

| | | |
|---|---|---|
| CN | 103204846 A | 7/2013 |
| CN | 104170111 A | 11/2014 |
| KR | 10-2014-0038886 A | 3/2014 |
| KR | 1020140099082 A | 8/2014 |
| KR | 10-2015-0094398 A | 8/2015 |
| KR | 10-2016-0026744 A | 3/2016 |
| KR | 10-2016-0037734 A | 4/2016 |
| KR | 10-2016-0068683 A | 6/2016 |
| WO | 2015156587 A1 | 10/2015 |
| WO | 2015160224 A1 | 10/2015 |
| WO | 2015169412 A1 | 11/2015 |
| WO | 2016015810 A1 | 2/2016 |
| WO | 2016089165 A2 | 6/2016 |
| WO | 2016129672 A1 | 8/2016 |

* cited by examiner

ORGANIC LIGHT EMITTING ELEMENT

TECHNICAL FIELD

This application is a National Stage Application of International Application No. PCT/KR2017/007147 filed Jul. 5, 2017, and claims the benefit of Korean Patent Application No. 10-2016-0094936 filed Jul. 26, 2016, all of which are hereby incorporated by reference in their entirety for all purposes as if fully set forth herein.

The present specification relates to an organic light emitting device.

BACKGROUND ART

An organic light emission phenomenon is one of the examples of converting an electric current into visible rays through an internal process of a specific organic molecule. The principle of the organic light emission phenomenon is as follows. When an organic material layer is disposed between a anode and a cathode, if voltage is applied between internal parts of a specific organic molecule through the two electrodes, electrons and holes are injected into the organic material layer from the cathode and the anode, respectively. The electrons and the holes which are injected into the organic material layer are recombined to form an exciton, and the exciton falls down again to the ground state to emit light. An organic light emitting device using this principle may generally include an anode, a cathode, and an organic material layer disposed therebetween, for example, an organic material layer including a hole injection layer, a hole transporting layer, a light emitting layer, and an electron transporting layer.

An organic light emitting device means a self-emitting type device using an electroluminescence phenomenon in which light is emitted when an electric current flows through a luminescent organic compound, and has received attention as a next-generation material in various industrial fields such as a display and lighting. There is a need for developing a technology for increasing light emitting efficiency of an organic light emitting device by lowering a driving voltage of the organic light emitting device.

REFERENCES OF THE RELATED ART

Patent Documents

Korean Patent Application Laid-Open No. 2007-0076521

DISCLOSURE

Technical Problem

The present specification provides an organic light emitting device.

Technical Solution

An exemplary embodiment of the present specification provides an organic light emitting device including: an anode; a cathode disposed to face the anode; and a light emitting layer disposed between the anode and the cathode, in which the light emitting layer includes: a host including a P-type host and an N-type host, which produce an exciplex; and a phosphorescent dopant, and the host including the P-type host and the N-type host, which produce an exciplex, emits a photoluminescence light with a longer wavelength than a wavelength of each of the P-type host and the N-type host.

Advantageous Effects

The organic light emitting device according to an exemplary embodiment of the present specification has excellent light emitting efficiency by including a P-type host and an N-type host as a host of a light emitting layer to produce an exciplex, and has excellent efficiency of the organic light emitting device in terms of roll off.

MODE FOR INVENTION

Figure 1:
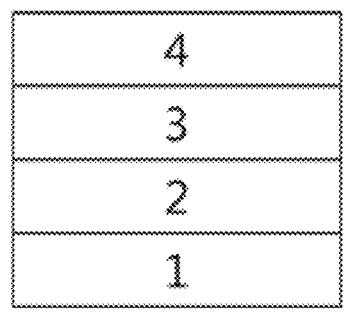
FIG. 1 illustrates an example of a stacking structure of an organic light emitting device according to an exemplary embodiment of the present specification.

Hereinafter, the present specification will be described in more detail.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

In the present specification, the term "production" means that a material having a new property and/or form is made by bonding two or more materials having different structures and/or characteristics to each other.

An exemplary embodiment of the present specification provides an organic light emitting device including: an anode; a cathode disposed to face the anode; and a light emitting layer disposed between the anode and the cathode, in which the light emitting layer includes: a host including a P-type host and an N-type host, which produce an exciplex; and a phosphorescent dopant, and the host including the P-type host and the N-type host, which produce an exciplex, emits a photoluminescence light with a longer wavelength than a wavelength of each of the P-type host and the N-type host.

According to an exemplary embodiment of the present specification, the P-type host may include an aromatic amine compound or a carbazole derivative as a hole transport type host.

According to an exemplary embodiment of the present specification, the P-type host is any one or more selected from compounds represented by the following Chemical Formulae 1 to 9.

[Chemical Formula 1]

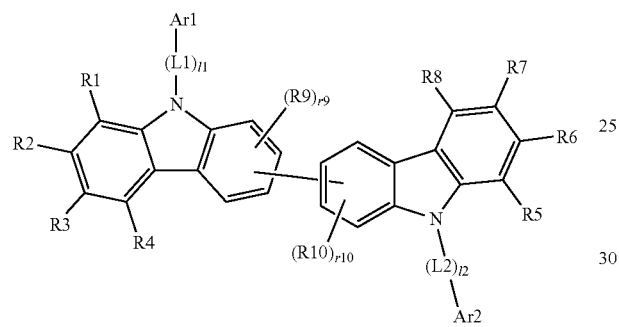

[Chemical Formula 2]

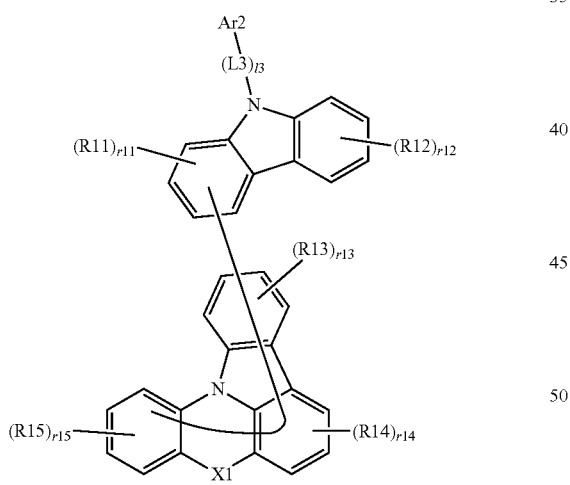

[Chemical Formula 3]

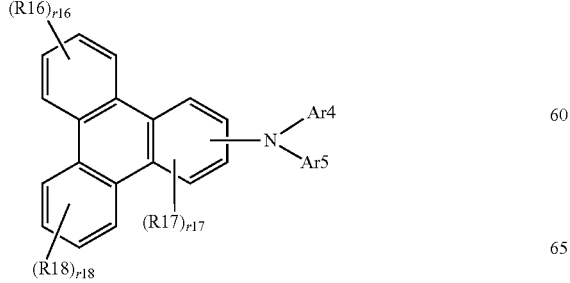

[Chemical Formula 4]

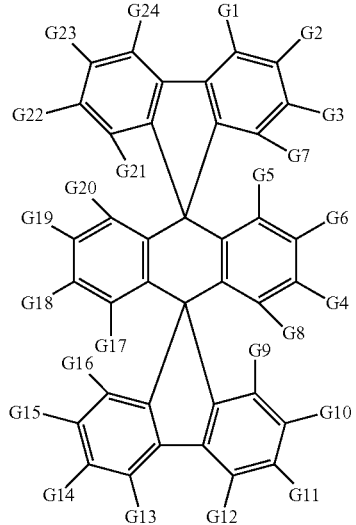

[Chemistry Formula 5]

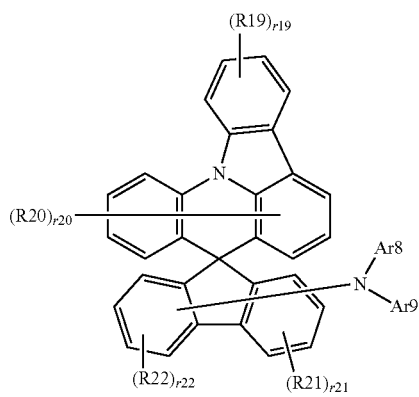

[Chemistry Formula 6]

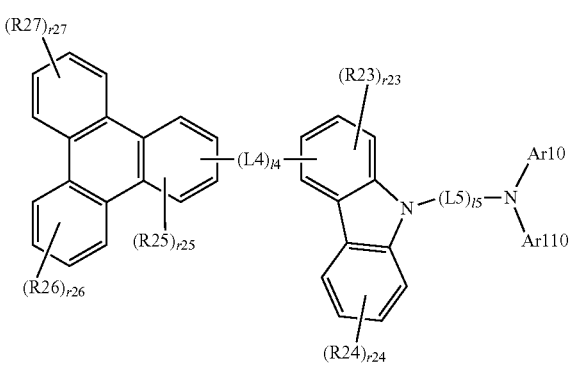

[Chemistry Formula 7]

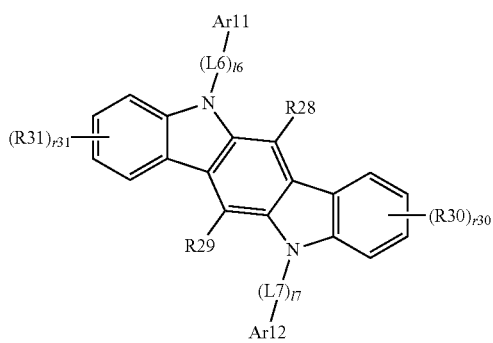

[Chemistry Formula 8]

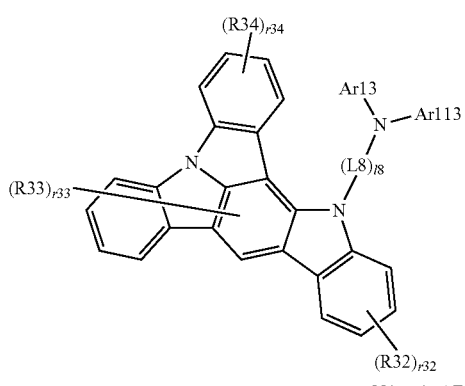

[Chemical Formula 9]

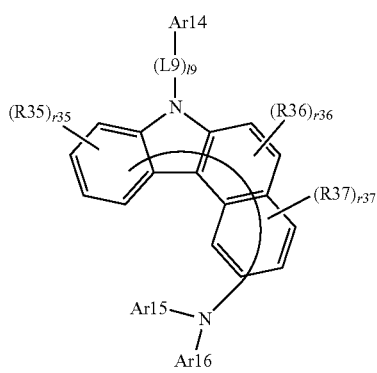

In Chemical Formulae 1 to 9,

X1 is O or S, at least one of G1 to G24 is

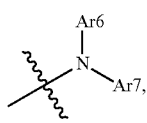

and the others are hydrogen,

L1 to L9 are the same as or different from each other, and are each independently a direct bond; or a substituted or unsubstituted arylene group, Ar1 to Ar16, Ar110, and Ar113 are the same as or different from each other, and are each independently a substituted or unsubstituted aryl group, R1 to R37 are the same as or different from each other, and are each independently hydrogen; a substituted or unsubstituted alkyl group; or a substituted or unsubstituted aryl group; or a substituted or unsubstituted carbazolyl group, or adjacent groups may be bonded to each other to form a substituted or unsubstituted ring, l1 to l9 are each 1 or 2, when l1 to l9 are each a plural number, a plurality of structures in the parenthesis are the same as or different from each other, r36 is 1 or 2, r9, r10, r11, r14, r17, r23, and r25 are each 1 to 3, r12, r13, r15, r16, r18, r19, r21, r22, r24, r26, r27, r30, r31, r32, r34, r35, and r37 are each 1 to 4, r33 is 1 to 5, r20 is 1 to 7, $3 \leq r13+r14+r15 \leq 10$, $2 \leq r21+\leq r22 \leq 7$, $3 \leq r35+r36+r37 \leq 9$, and when r9 to r27 and r30 to r37 are each a plural number, a plurality of structures in the parentheses are the same as or different from each other.

According to an exemplary embodiment of the present specification, the N-type host may include a n-electron lack-type heteroaryl compound or a triazine derivative compound as an electron transport type host. The n-electron lack-type heteroaryl compound is a compound including a heteroaryl group, and means a compound in which the electron density of the non-localized n-bond of the heteroaryl group is lowered due to the high electron affinity of the heteroatom, and the like.

According to an exemplary embodiment of the present specification, the N-type host is any one or more selected from compounds represented by the following Chemical Formulae 10 to 13.

[Chemical Formula 10]

[Chemical Formula 11]

[Chemical Formula 12]

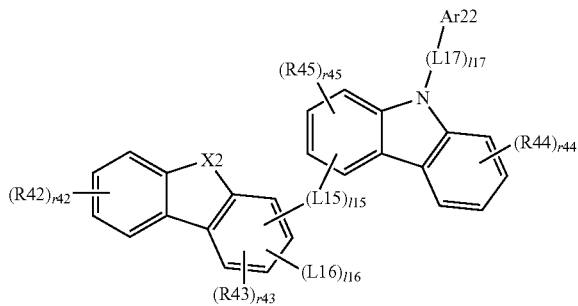

[Chemical Formula 13]

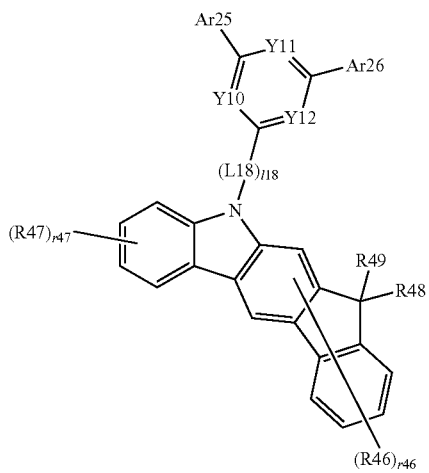

In Chemical Formulae 10 to 13,

X2 is O or S, at least one of Y1 to Y3 is N, and the others are CH, at least one of Y7 to Y9 is N, and the others are CH, at least one of Y10 to Y12 is N, and the others are CH, at least one of Q1 to Q9 is

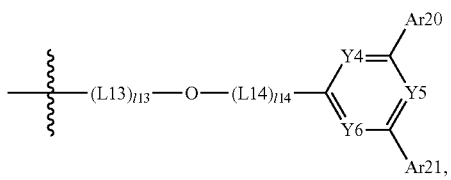

and the others are hydrogen;

a substituted or unsubstituted aryl group; or a substituted or unsubstituted heteroaryl group, at least one of Y4 to Y6 is N, and the others are CH, L10 to L18 are the same as or different from each other, and are each independently a direct bond; or a substituted or unsubstituted arylene group, Ar17 to Ar26 are the same as or different from each other, and are each independently a substituted or unsubstituted aryl group, R38 to R49 are the same as or different from each other, and are each independently hydrogen; a substituted or unsubstituted alkyl group; a substituted or unsubstituted aryl group; or a substituted or unsubstituted carbazolyl group, or adjacent groups may be bonded to each other to form a substituted or unsubstituted ring, 110 to 118 are each 1 or 2, when 110 to 118 are each a plural number, a plurality of structures in the parenthesis are the same as or different from each other, r43 is 1 or 2, r38, r41, and r45 are each 1 to 3, r39, r40, r42, r44, and r47 are each 1 to 4, r46 is 1 to 6, and when r38 to r47 are each a plural number, a plurality of structures in the parenthesis are the same as or different from each other.

According to an exemplary embodiment of the present specification, the P-type host is any one or more selected from the compounds represented by Chemical Formulae 1 to 9, and the N-type host is any one or more selected from the compounds represented by Chemical Formulae 10 to 13.

According to another exemplary embodiment of the present specification, the P-type host is any one selected from the compounds represented by Chemical Formulae 1 to 9, and the N-type host is any one selected from the compounds represented by Chemical Formulae 10 to 13.

According to still another exemplary embodiment of the present specification, the P-type host is the compound represented by Chemical Formula 1, and the N-type host is the compound represented by Chemical Formula 10.

According to yet another exemplary embodiment of the present specification, the P-type host is the compound represented by Chemical Formula 1, and the N-type host is the compound represented by Chemical Formula 11.

According to still yet another exemplary embodiment of the present specification, the P-type host is the compound represented by Chemical Formula 1, and the N-type host is the compound represented by Chemical Formula 12.

According to a further exemplary embodiment of the present specification, the P-type host is any one selected from the compounds represented by Chemical Formulae 1 to 9, and the N-type host is any one selected from the compounds represented by Chemical Formulae 10 to 12.

According to another further exemplary embodiment of the present specification, the P-type host is any one selected from the compounds represented by Chemical Formulae 2 to 9, and the N-type host is any one selected from the compounds represented by Chemical Formulae 10 to 13.

According to an exemplary embodiment of the present specification, the host including the P-type host and the N-type host, which produce an exciplex, emits a photoluminescence light with a longer wavelength than a wavelength of each of the P-type host and the N-type host.

According to an exemplary embodiment of the present specification, a photoluminescence peak of the host including the P-type host and the N-type host, which produce an exciplex, has lower photon energy than a photon energy of each photoluminescence peak of the P-type host and the N-type host.

The host including the P-type host and the N-type host, which produce an exciplex, emits a photoluminescence light with a longer wavelength than a wavelength of each of the P-type host and the N-type host, and thus has low photon energy. Accordingly, the exciplex produced from the host is easily transferred to a dopant, and as a result, a roll-off phenomenon of an organic light emitting device, in which the host including the P-type host and the N-type host, which produce the exciplex, according to an exemplary embodiment of the present specification is included in a light emitting layer, is reduced, and the device has excellent efficiency.

Specifically, since for the exciplex, an exciton produced when two different molecules (a P-type host and an N-type host) are adjacent to each other is produced over the two molecules, the distance between the hole and the electron, which produce the exciton, becomes physically long, so that the binding energy is lowered. As a result, holes and electrons in a hole transporting layer or an electron transporting layer, which are injected into a light emitting layer to the host, which forms an exciplex, according to an exemplary embodiment of the present specification is applied, easily enter the host in which the exciplex is formed, as compared to the host of the light emitting layer in which the exciplex is not formed (Adv. Funct. Mater. 2013, 23, 4913; Adv. Funct. Mater. 2014, 24, 4681).

In general, the light emission mechanism of the organic light emitting device in which the exciplex is not formed is mainly a trap assisted recombination in which holes are first trapped in the dopant of the light emitting layer, and form an exciton with electrons introduced later through the host, and in this case, since the life time of the exciton formed in the dopant is long and the moving distance thereof is long, there easily occurs a process in which excitons collide with each other and thus are annihilated, and the process is known to be responsible for causing the roll-off in a general phosphorescence emission.

However, since the exciplex of the organic light emitting device according to an exemplary embodiment of the present specification uses a Langevin recombination in which exciplex energy is transferred to a dopant, instead of the Dexter electron exchange (Dexter mechanism) as in the aforementioned case, the energy is efficiently transferred to the light emitting dopant, and a problem caused by the roll-off is also decreased. The reason why a deterioration in efficiency of the device caused by an exciton quench between hosts (P-type host and N-type host) in which the exciplex is formed or the roll-off is not problematic is that an exciplex is an exciton over the two different molecules (P-type host and N-type host), and thus a condition for which the exciton moves is stricter, and as a result, the exciplex does not move, and the rate of the energy transfer is much faster than that of the electron exchange through the Langevin recombination, so that it is possible to expect to improve efficiency of a device and evade a roll-off problem (Adv. Funct. Mater. 2013, 23, 4913; Adv. Funct. Mater. 2014, 24, 4681; Discuss Faraday Soc. 1959, 7, 27).

According to an exemplary embodiment of the present specification, the HOMO energy level of the P-type host is higher than the HOMO energy level of the N-type host, and the LUMO energy level of the N-type host is lower than the LUMO energy level of the P-type host. Accordingly, since excited electrons are positioned in the LUMO of the N-type host, and holes are positioned in the HOMO of the P-type host, electrons and holes positioned in the two different molecules, respectively, interact with each other, and as a result, the exciplex is produced.

In the present specification, the energy level means a size of energy. Accordingly, even when the energy level is expressed in a negative (−) direction from a vacuum level, it is interpreted that the energy level means an absolute value of the corresponding energy value. For example, the HOMO energy level means a distance from the vacuum level to the highest occupied molecular orbital. Further, the LUMO energy level means a distance from the vacuum level to the lowest unoccupied molecular orbital.

For measuring the HOMO energy level in the present specification, it is possible to use a UV photoelectron spectroscopy (UPS) for measuring an ionization potential of a material by irradiating UV on a surface of a thin film and detecting electrons jumping out in this case. Otherwise, for measuring the HOMO energy level, it is possible to use a cyclic voltammetry (CV) for dissolving a material to be measured along with an electrolytic solution in a solvent, and then measuring an oxidation potential through voltage sweep. Furthermore, it is possible to use a method of photoemission yield spectrometer in air (PYSA), which measures an ionization potential in the atmosphere, by using a machine of AC-3 (manufactured by RKI Instruments, Inc.).

Specifically, the HOMO energy level of the present specification was measured by vacuum depositing a target material to have a thickness of 50 nm or more on an ITO substrate, and then using an AC-3 measuring instrument (manufactured by RKI Instruments, Inc.). Further, for the LUMO energy level, an absorption spectrum (abs.) and a photoluminescence spectrum (PL) of the sample prepared above were measured, and then each spectrum edge energy was calculated, the difference was taken as a bandgap (Eg), and the LUMO energy level was calculated as a value obtained by subtracting the bandgap difference from the HOMO energy level measured from the AC-3.

In the present specification, the LUMO energy level may be obtained through inverse photoelectron spectroscopy (IPES) or the measurement of electrochemical reduction potential. The IPES is a method of determining the LUMO energy level by irradiating electron beam on a thin film, and measuring light emitting at this time. In addition, in the measurement of electrochemical reduction potential, a measurement target material is dissolved along with the electrolytic solution in a solvent, and then a reduction potential may be measured through voltage sweep. Otherwise, the LUMO energy level may be calculated by using the HOMO energy level and a singlet energy level obtained by measuring a UV absorption degree of the target material.

According to an exemplary embodiment of the present specification, the host includes the P-type host:the N-type host at a weight ratio of 2:8 to 8:2, preferably at a weight ratio of 3:7 to 7:3.

When the P-type host and the N-type host are included in the ratio range, electrons and holes positioned in the P-type host and the N-type host interact with each other to optimize production of the exciplex.

According to an exemplary embodiment of the present specification, the efficiency ratio of the organic light emitting device according to a change in current density is 1.6 or less, preferably 1.5 or less.

Since an organic light emitting device satisfying the efficiency ratio has a small change width in current density according to the current change, the stability of the organic light emitting device is high.

Further, since the organic light emitting device according to the present invention satisfies the efficiency ratio, a reduction width in power consumption is decreased as compared to the organic light emitting device in the related art, which includes a host that does not produce the exciplex, and as a result, there is an effect in that an amount of electricity used is reduced, and the service life of the device is improved.

The efficiency ratio may be calculated as a ratio of the highest efficiency (max·cd/A) to the efficiency (cd/A (at 100 mA/cm$^2$)) at 100 mA/cm$^2$, which exhibits the lowest efficiency as in the following Equation 1, by measuring the efficiency according to the change in current density of 0.01 mA/cm$^2$ to 100 mA/cm$^2$.

Efficiency ratio=(max·cd/A)/(cd/A(at 100 mA/cm$^2$))  [Equation 1]

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more substituents are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a bonding portion. In the present specification, a halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

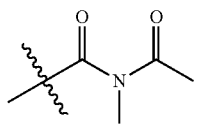 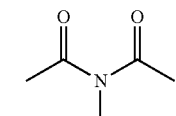

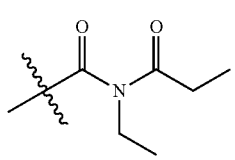 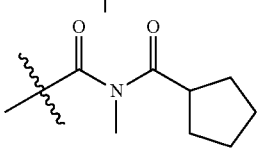

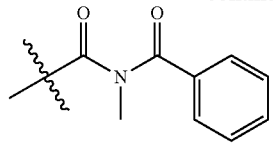

In the present specification, for an amide group, the nitrogen of the amide group may be substituted with hydrogen, a straight, branched, or cyclic alkyl group having 1 to 30 carbon atoms, or an aryl group having 6 to 30 carbon atoms. Specifically, the amide group may be a compound having the following structural formulae, but is not limited thereto.

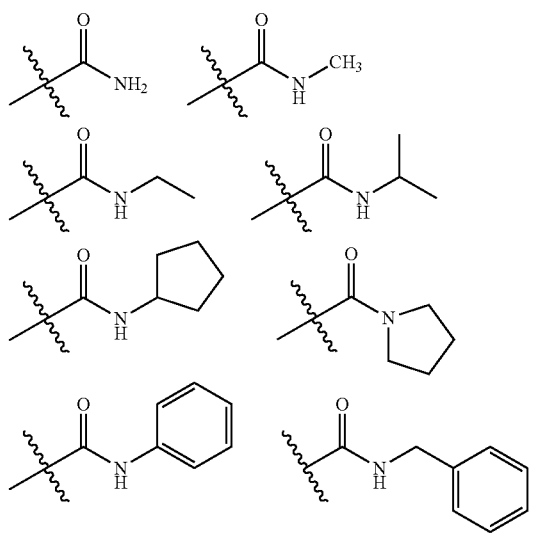

In the present specification, the number of carbon atoms of a carbonyl group is not particularly limited, but is preferably 1 to 30. Specifically, the carbonyl group may be a compound having the following structures, but is not limited thereto.

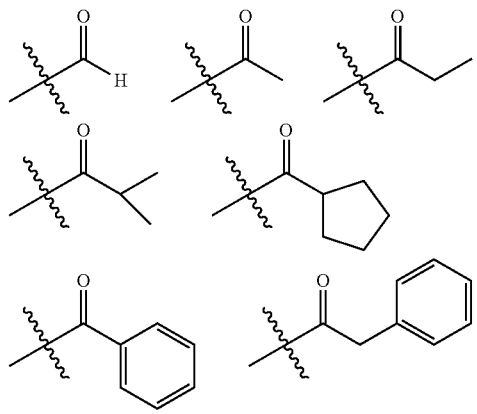

In the present specification, for an ester group, the oxygen of the ester group may be substituted with a straight, branched, or cyclic alkyl group having 1 to 25 carbon atoms, or an aryl group having 6 to 30 carbon atoms. Specifically, the ester group may be a compound having the following structural formulae, but is not limited thereto.

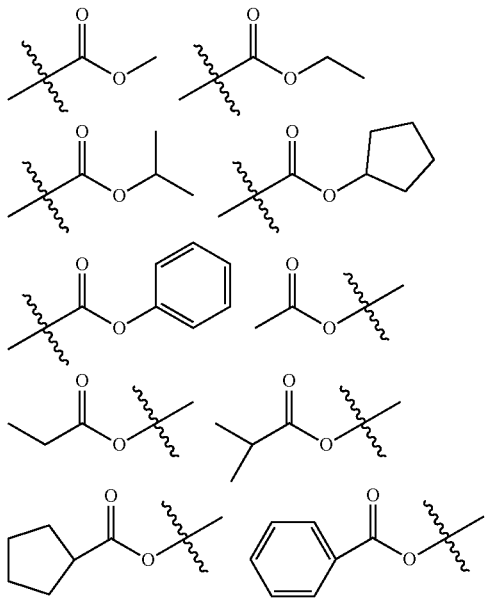

In the present specification, the alkyl group may be straight or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the haloalkyl group means an alkyl group substituted with a halogen group, and the definitions of the halogen group and the alkyl group are the same as those described above.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —$NH_2$; an alkylamine group; an N-arylalkylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, and the like, but are not limited thereto.

In the present specification, an N-alkylarylamine group means an amine group in which an alkyl group and an aryl group are substituted with N of the amine group. In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group may be straight or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto. In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be —$BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. The polycyclic aryl group is dicyclic or tricyclic or more, and specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

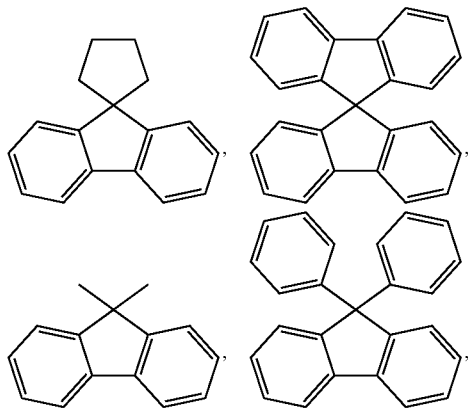

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of a heterocyclic group include a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), an isoxazolyl group, a thiadiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, the heterocyclic group may be monocyclic or polycyclic, may be an aromatic ring, an aliphatic ring, or a fused ring of the aromatic ring and the aliphatic ring, and may be selected from the examples of the heteroaryl group.

In the present specification, an arylene group means a group having two bonding positions in an aryl group, that is, a divalent group. The above-described description on the aryl group may be applied to the arylene group, except for a divalent arylene group.

In the present specification, in a substituted or unsubstituted ring formed by bonding adjacent groups, the "ring" means a substituted or unsubstituted hydrocarbon ring; or a substituted or unsubstituted hetero ring. In the present specification, a ring means a substituted or unsubstituted hydrocarbon ring; or a substituted or unsubstituted hetero ring.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more atoms other than carbon, that is, one or more heteroatoms, and specifically, the heteroatom may include one or more atoms selected from the group consisting of O, N, Se, and S, and the like. The hetero ring may be monocyclic or polycyclic, may be an aromatic ring, an aliphatic ring, or a fused ring of the aromatic ring and the aliphatic ring, and may be selected from the examples of the heteroaryl group or the heterocyclic group, except for the hetero ring which is not monovalent.

According to an exemplary embodiment of the present specification, Chemical Formula 1 is represented by the following Chemical Formula 1-1 or 1-2.

[Chemical Formula 1-1]

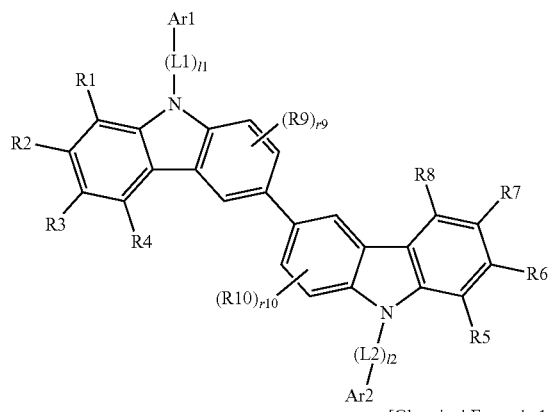

[Chemical Formula 1-2]

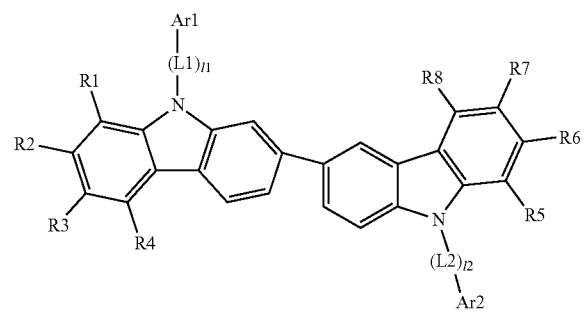

In Chemical Formulae 1-1 and 1-2, the definitions of R1 to R10, r9, r10, L1, L2, Ar1, Ar2, l1, and l2 are the same as those in Chemical Formula 1.

According to an exemplary embodiment of the present specification, in Chemical Formula 1, R1 to R10 are the same as or different from each other, and are each independently hydrogen; a substituted or unsubstituted aryl group; or a substituted or unsubstituted carbazolyl group.

According to an exemplary embodiment of the present specification, in Chemical Formula 1, R1 to R10 are the same as or different from each other, and are each independently hydrogen; or a carbazolyl group unsubstituted or substituted with an aryl group.

According to an exemplary embodiment of the present specification, in Chemical Formula 1, R1 to R10 are the same as or different from each other, and are each independently hydrogen; or a carbazolyl group unsubstituted or substituted with a phenyl group.

According to an exemplary embodiment of the present specification, in Chemical Formula 1, adjacent groups in R1 to R10 are bonded to each other to form a substituted or unsubstituted ring.

According to an exemplary embodiment of the present specification, in Chemical Formula 1, adjacent groups in R1 to R10 are bonded to each other to form a substituted or unsubstituted aromatic ring.

According to an exemplary embodiment of the present specification, in Chemical Formula 1, adjacent groups in R1 to R10 are bonded to each other to form a substituted or unsubstituted indene ring.

According to an exemplary embodiment of the present specification, in Chemical Formula 1, adjacent groups in R1 to R10 are bonded to each other to form an indene ring substituted with a methyl group.

According to an exemplary embodiment of the present specification, in Chemical Formula 1, R2 and R3; or R6 and R7 are bonded to each other to form an indene ring substituted with a methyl group.

According to an exemplary embodiment of the present specification, in Chemical Formula 1, L1 and L2 are the same as or different from each other, and are each independently a direct bond; or a substituted or unsubstituted arylene group.

According to an exemplary embodiment of the present specification, in Chemical Formula 1, L1 and L2 are the same as or different from each other, and are each independently a direct bond; or an arylene group.

According to an exemplary embodiment of the present specification, in Chemical Formula 1, L1 and L2 are the same as or different from each other, and are each independently a direct bond; or a phenylene group.

According to an exemplary embodiment of the present specification, in Chemical Formula 1, Ar1 and Ar2 are the same as or different from each other, and are each independently a substituted or unsubstituted aryl group.

According to an exemplary embodiment of the present specification, in Chemical Formula 1, Ar1 and Ar2 are the same as or different from each other, and are each independently an aryl group.

According to an exemplary embodiment of the present specification, in Chemical Formula 1, Ar1 and Ar2 are the same as or different from each other, and are each independently a phenyl group; a biphenyl group; a terphenyl group; a naphthyl group; or a phenanthrenyl group.

According to an exemplary embodiment of the present specification, Chemical Formula 2 is represented by any one of the following Chemical Formulae 2-1 to 2-3.

[Chemical Formula 2-1]

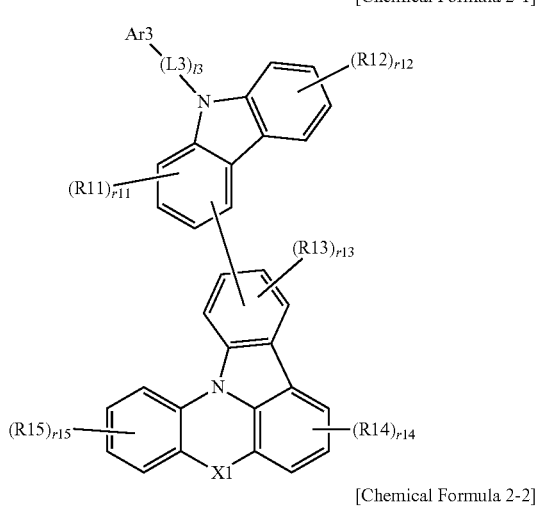

[Chemical Formula 2-2]

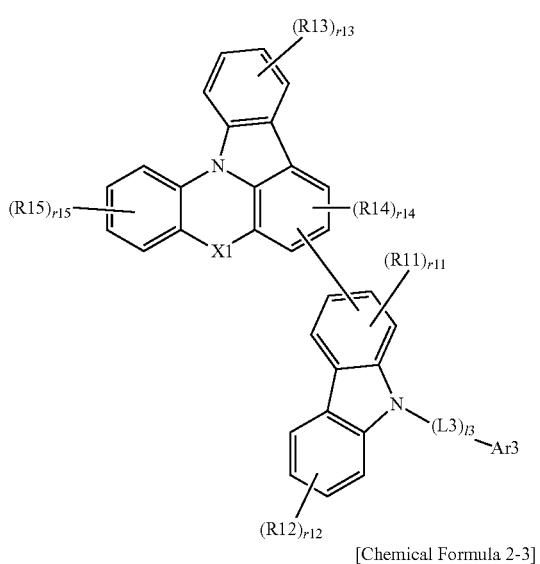

[Chemical Formula 2-3]

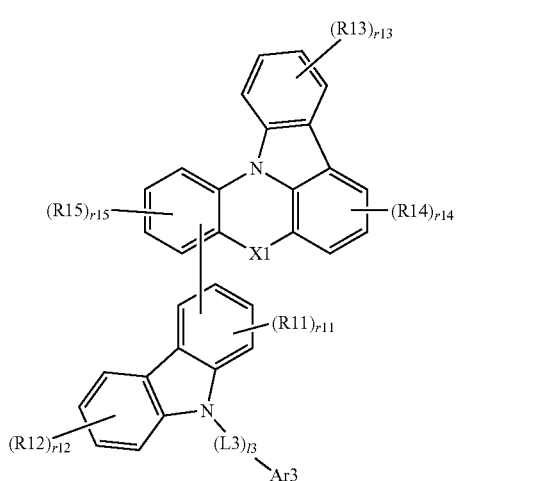

In Chemical Formulae 2-1 to 2-3,
the definitions of X1, R11 to R15, r11 to r15, L3, l3, and Ar3 are the same as those in Chemical Formula 2.

According to an exemplary embodiment of the present specification, in Chemical Formula 2, X1 is O.

According to an exemplary embodiment of the present specification, in Chemical Formula 2, L3 is a direct bond; or a substituted or unsubstituted arylene group.

According to an exemplary embodiment of the present specification, in Chemical Formula 2, L3 is a direct bond; or an arylene group.

According to an exemplary embodiment of the present specification, in Chemical Formula 2, L3 is a direct bond; or a phenylene group.

According to an exemplary embodiment of the present specification, in Chemical Formula 2, Ar3 is a substituted or unsubstituted aryl group.

According to an exemplary embodiment of the present specification, in Chemical Formula 2, Ar3 is an aryl group.

According to an exemplary embodiment of the present specification, in Chemical Formula 2, Ar3 is a phenyl group; or a biphenyl group.

According to an exemplary embodiment of the present specification, Chemical Formula 3 is represented by the following Chemical Formula 3-1.

[Chemical Formula 3-1]

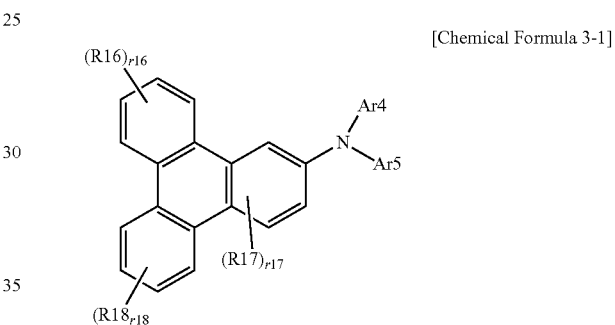

In Chemical Formula 3-1, the definitions of R16 to R18, r16 to r18, Ar4, and Ar5 are the same as those in Chemical Formula 3.

According to an exemplary embodiment of the present specification, in Chemical Formula 3, Ar4 and Ar5 are the same as or different from each other, and are each independently a substituted or unsubstituted aryl group.

According to an exemplary embodiment of the present specification, in Chemical Formula 3, Ar4 and Ar5 are the same as or different from each other, and are each independently an aryl group unsubstituted or substituted with an alkyl group.

According to an exemplary embodiment of the present specification, in Chemical Formula 3, Ar4 and Ar5 are the same as or different from each other, and are each independently a biphenyl group; a terphenyl group; or a fluorenyl group substituted with an alkyl group.

According to an exemplary embodiment of the present specification, in Chemical Formula 3, Ar4 and Ar5 are the same as or different from each other, and are each independently a biphenyl group; a terphenyl group; or a fluorenyl group substituted with a methyl group.

According to an exemplary embodiment of the present specification, Chemical Formula 4 is represented by the following Chemical Formula 4-1 or 4-2.

[Chemical Formula 4-1]

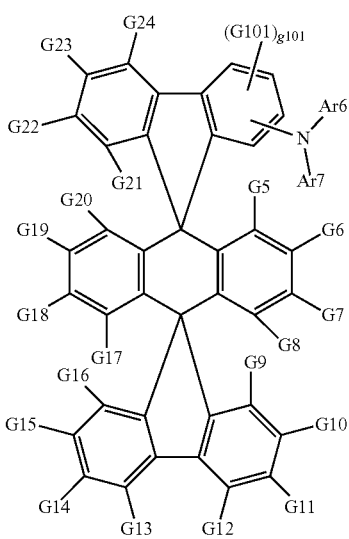

[Chemical Formula 4-2]

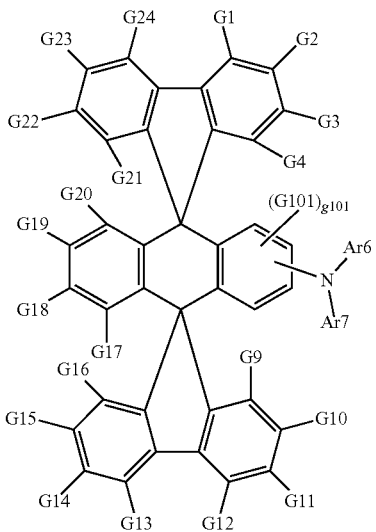

In Chemical Formulae 4-1 and 4-2, the definitions of G1 to G24, Ar6, and Ar7 are the same as those in Chemical Formula 4, G101 is hydrogen; and g101 is an integer from 1 to 3.

According to an exemplary embodiment of the present specification, in Chemical Formula 4, at least one of G1 to G24 is

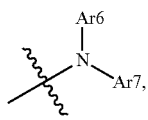

and the others are hydrogen, and Ar6 and Ar7 are the same as or different from each other, and are each independently a substituted or unsubstituted aryl group.

According to an exemplary embodiment of the present specification, Ar6 and Ar7 are the same as or different from each other, and are each independently an aryl group substituted with an alkyl group; an aryl group substituted with a heteroaryl group; or an aryl group.

According to an exemplary embodiment of the present specification, Ar6 and Ar7 are the same as or different from each other, and are each independently a fluorenyl group substituted with an alkyl group; a phenyl group substituted with a heteroaryl group; or a biphenyl group.

According to an exemplary embodiment of the present specification, Ar6 and Ar7 are the same as or different from each other, and are each independently a fluorenyl group substituted with a methyl group; a phenyl group substituted with a dibenzofuranyl group; or a biphenyl group.

According to an exemplary embodiment of the present specification, Chemical Formula 5 is represented by the following Chemical Formula 5-1.

[Chemical Formula 5-1]

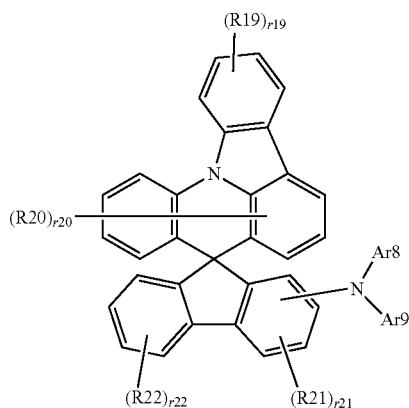

In Chemical Formula 5-1, the definitions of R19 to R22, r19 to r22, Ar8, and Ar9 are the same as those in Chemical Formula 5.

According to an exemplary embodiment of the present specification, in Chemical Formula 5, Ar8 and Ar9 are the same as or different from each other, and are each independently a substituted or unsubstituted aryl group.

According to an exemplary embodiment of the present specification, in Chemical Formula 5, Ar8 and Ar9 are the same as or different from each other, and are each independently an aryl group substituted with a heteroaryl group; or an aryl group.

According to an exemplary embodiment of the present specification, in Chemical Formula 5, Ar8 and Ar9 are the same as or different from each other, and are each independently a phenyl group substituted with a dibenzofuranyl group; or a biphenyl group.

According to an exemplary embodiment of the present specification, Chemical Formula 6 is represented by the following Chemical Formula 6-1.

[Chemical Formula 6-1]

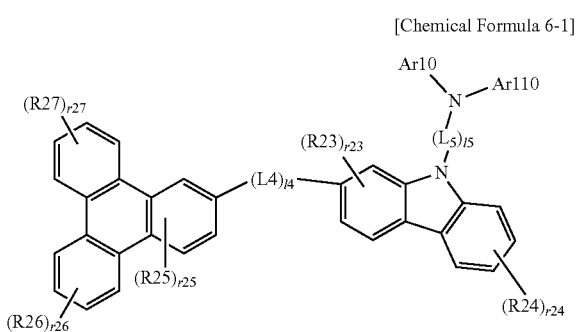

In Chemical Formula 6-1, the definitions of R23 to R27, r23 to r27, L4, L5, l4, l5, Ar10, and Ar110 are the same as those in Chemical Formula 6.

According to an exemplary embodiment of the present specification, in Chemical Formula 6, L4 and L5 are the same as or different from each other, and are each independently a substituted or unsubstituted arylene group.

According to an exemplary embodiment of the present specification, in Chemical Formula 6, L4 and L5 are the same as or different from each other, and are each independently an arylene group.

According to an exemplary embodiment of the present specification, in Chemical Formula 6, L4 and L5 are a phenylene group.

According to an exemplary embodiment of the present specification, in Chemical Formula 6, Ar10 and Ar110 are the same as or different from each other, and are each independently a substituted or unsubstituted aryl group.

According to an exemplary embodiment of the present specification, in Chemical Formula 6, Ar10 and Ar110 are the same as or different from each other, and are each independently an aryl group.

According to an exemplary embodiment of the present specification, in Chemical Formula 6, Ar10 and Ar110 are a phenyl group.

According to an exemplary embodiment of the present specification, in Chemical Formula 7, R28 and R29 are the same as or different from each other, and are each independently a substituted or unsubstituted aryl group.

According to an exemplary embodiment of the present specification, in Chemical Formula 7, R28 and R29 are the same as or different from each other, and are each independently an aryl group.

According to an exemplary embodiment of the present specification, in Chemical Formula 7, R28 and R29 are a phenyl group.

According to an exemplary embodiment of the present specification, in Chemical Formula 7, L6 and L7 are the same as or different from each other, and are each independently a direct bond; or a substituted or unsubstituted arylene group.

According to an exemplary embodiment of the present specification, in Chemical Formula 7, L6 and L7 are the same as or different from each other, and are each independently a direct bond; or an arylene group.

According to an exemplary embodiment of the present specification, in Chemical Formula 7, L6 and L7 are the same as or different from each other, and are each independently a direct bond; or a phenylene group.

According to an exemplary embodiment of the present specification, in Chemical Formula 7, Ar11 and Ar12 are the same as or different from each other, and are each independently a substituted or unsubstituted aryl group.

According to an exemplary embodiment of the present specification, in Chemical Formula 7, Ar11 and Ar12 are the same as or different from each other, and are each independently an aryl group.

According to an exemplary embodiment of the present specification, in Chemical Formula 7, Ar11 and Ar12 are the same as or different from each other, and are each independently a phenyl group; or a biphenyl group.

According to an exemplary embodiment of the present specification, in Chemical Formula 8 is a direct bond; or an arylene group.

According to an exemplary embodiment of the present specification, in Chemical Formula 8 is a direct bond; or a phenylene group.

According to an exemplary embodiment of the present specification, in Chemical Formula 8, Ar13 and Ar113 are the same as or different from each other, and are each independently a substituted or unsubstituted aryl group.

According to an exemplary embodiment of the present specification, in Chemical Formula 8, Ar13 and Ar113 are the same as or different from each other, and are each independently an aryl group.

According to an exemplary embodiment of the present specification, in Chemical Formula 8, Ar13 and Ar113 are a biphenyl group.

According to an exemplary embodiment of the present specification, Chemical Formula 9 is represented by any one of the following Chemical Formulae 9-1 to 9-3.

[Chemical Formula 9-1]

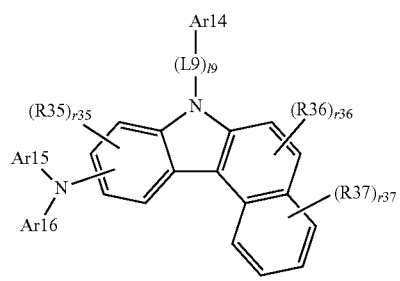

[Chemical Formula 9-2]

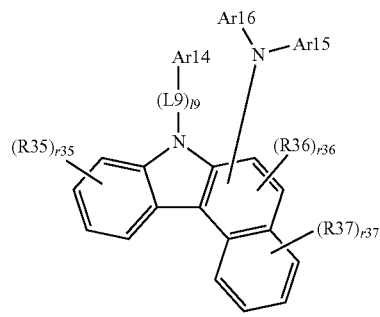

[Chemical Formula 9-3]

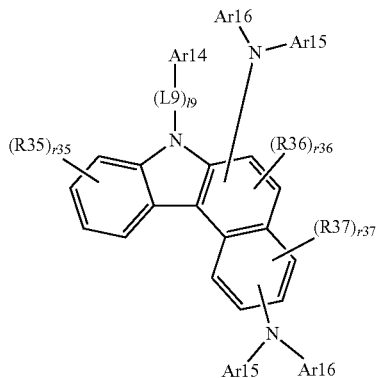

In Chemical Formulae 9-1 to 9-3,
the definitions of R35 to R37, r35 to r37, L9, l9, and Ar14 to Ar16 are the same as those in Chemical Formula 9.

According to an exemplary embodiment of the present specification, in Chemical Formula 9, L9 is a direct bond; or a substituted or unsubstituted arylene group.

According to an exemplary embodiment of the present specification, in Chemical Formula 9, L9 is a direct bond; or an arylene group.

According to an exemplary embodiment of the present specification, in Chemical Formula 9, L9 is a direct bond; or a phenylene group.

According to an exemplary embodiment of the present specification, in Chemical Formula 9, Ar14 to Ar16 are the same as or different from each other, and are each independently a substituted or unsubstituted aryl group.

According to an exemplary embodiment of the present specification, in Chemical Formula 9, Ar14 to Ar16 are the same as or different from each other, and are each independently an aryl group unsubstituted or substituted with an alkyl group.

According to an exemplary embodiment of the present specification, in Chemical Formula 9, Ar14 to Ar16 are the same as or different from each other, and are each independently a biphenyl group; or a fluorenyl group substituted with a methyl group.

According to an exemplary embodiment of the present specification, Chemical Formula 10 is represented by the following Chemical Formula 10-1.

[Chemical Formula 10-1]

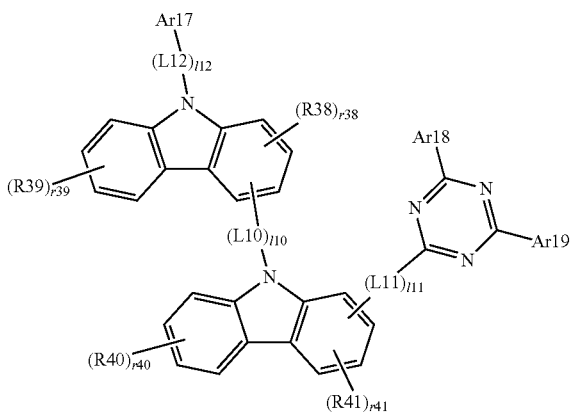

In Chemical Formula 10-1,
the definitions of R38 to R41, L10 to L12, l10 to l12, and Ar17 to Ar19 are the same as those in Chemical Formula 10.

According to an exemplary embodiment of the present specification, in Chemical Formula 10, L10 to L12 are the same as or different from each other, and are each independently a direct bond; or a substituted or unsubstituted arylene group.

According to an exemplary embodiment of the present specification, in Chemical Formula 10, L10 to L12 are the same as or different from each other, and are each independently a direct bond; or an arylene group.

According to an exemplary embodiment of the present specification, in Chemical Formula 10, L10 to L12 are the same as or different from each other, and are each independently a direct bond; or a phenylene group.

According to an exemplary embodiment of the present specification, in Chemical Formula 10, Ar17 to Ar19 are the same as or different from each other, and are each independently a substituted or unsubstituted aryl group.

According to an exemplary embodiment of the present specification, in Chemical Formula 10, Ar17 to Ar19 are the same as or different from each other, and are each independently an aryl group.

According to an exemplary embodiment of the present specification, in Chemical Formula 10, Ar17 to Ar19 are the same as or different from each other, and are each independently a phenyl group; or a biphenyl group.

According to an exemplary embodiment of the present specification, Chemical Formula 11 is represented by the following Chemical Formula 11-1 or 11-2.

[Chemical Formula 11-1]

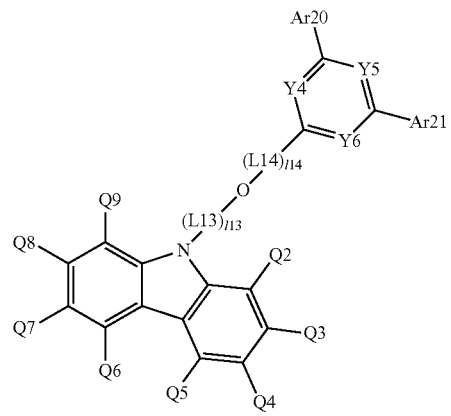

[Chemical Formula 11-2]

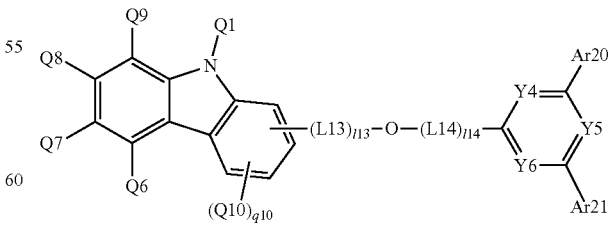

In Chemical Formulae 11-1 and 11-2,
the definitions of Q1 to Q9, Y4 to Y6, L13, L14, l13, l14, Ar20, and Ar21 are the same as those in Chemical Formula 11, Q10 is hydrogen; a substituted or unsubstituted aryl group; or a substituted or unsubstituted heteroaryl group, q10 is an integer from 1 to 3, when q10 is 2 or more, two or more Q10's are the same as or different from each other.

According to an exemplary embodiment of the present specification, in Chemical Formula 11, at least one of Q1 to Q9 is

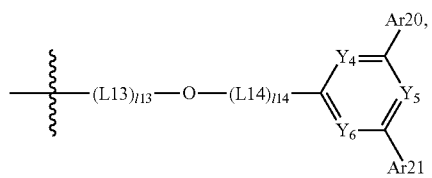

and the others are hydrogen; an aryl group; or a heteroaryl group.

According to an exemplary embodiment of the present specification, in Chemical Formula 11, at least one of Q1 to Q9 is

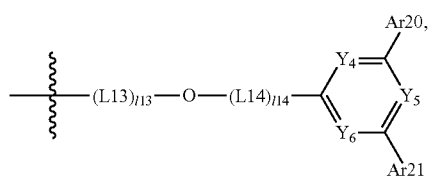

and the others are hydrogen; a phenyl group; or a dibenzofuranyl group.

According to an exemplary embodiment of the present specification, Y4 to Y6 are N.

According to an exemplary embodiment of the present specification, L13 and L14 are the same as or different from each other, and are each independently a direct bond; or a substituted or unsubstituted arylene group.

According to an exemplary embodiment of the present specification, L13 and L14 are the same as or different from each other, and are each independently a direct bond; or an arylene group.

According to an exemplary embodiment of the present specification, L13 and L14 are the same as or different from each other, and are each independently a direct bond; a phenylene group; or a biphenylylene group.

According to an exemplary embodiment of the present specification, Ar20 and Ar21 are the same as or different from each other, and are each independently a substituted or unsubstituted aryl group.

According to an exemplary embodiment of the present specification, Ar20 and Ar21 are the same as or different from each other, and are each independently an aryl group.

According to an exemplary embodiment of the present specification, Ar20 and Ar21 are the same as or different from each other, and are each independently a phenyl group.

According to an exemplary embodiment of the present specification, Chemical Formula 12 is represented by the following Chemical Formula 12-1.

[Chemical Formula 12-1]

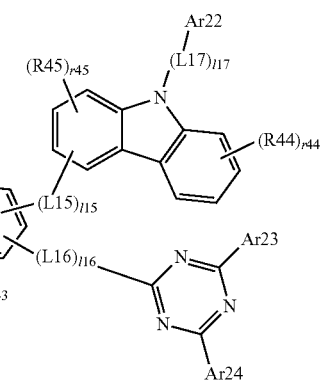

In Chemical Formula 12-1, the definitions of R42 to R45, r42 to r45, L15 to L17, l15 to l17, and Ar22 to Ar24 are the same as those in Chemical Formula 12.

According to an exemplary embodiment of the present specification, in Chemical Formula 12, L15 to L17 are the same as or different from each other, and are each independently a direct bond; or a substituted or unsubstituted arylene group.

According to an exemplary embodiment of the present specification, in Chemical Formula 12, L15 to L17 are the same as or different from each other, and are each independently a direct bond; or an arylene group.

According to an exemplary embodiment of the present specification, in Chemical Formula 12, L15 to L17 are a direct bond.

According to an exemplary embodiment of the present specification, in Chemical Formula 12, Ar22 to Ar24 are the same as or different from each other, and are each independently a substituted or unsubstituted aryl group.

According to an exemplary embodiment of the present specification, in Chemical Formula 12, Ar22 to Ar24 are the same as or different from each other, and are each independently an aryl group.

According to an exemplary embodiment of the present specification, in Chemical Formula 12, Ar22 to Ar24 are the same as or different from each other, and are each independently a phenyl group.

According to an exemplary embodiment of the present specification, Chemical Formula 13 is represented by the following Chemical Formula 13-1.

[Chemical Formula 13-1]

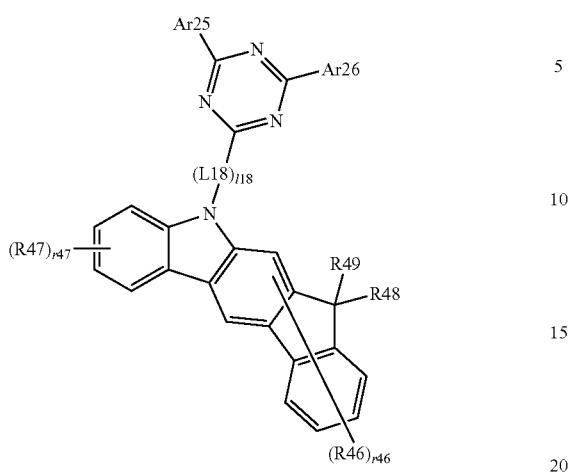

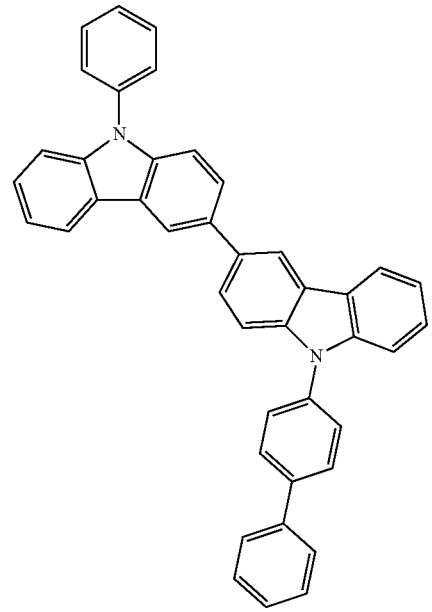
1-1

In Chemical Formula 13-1, the definitions of R46 to R49, r46, r47, L18, l18, Ar25, and Ar26 are the same as those in Chemical Formula 13.

According to an exemplary embodiment of the present specification, in Chemical Formula 13, R48 and R49 are the same as or different from each other, and are each independently a substituted or unsubstituted alkyl group.

According to an exemplary embodiment of the present specification, in Chemical Formula 13, R48 and R49 are the same as or different from each other, and are each independently an alkyl group.

According to an exemplary embodiment of the present specification, in Chemical Formula 13, R48 and R49 are the same as or different from each other, and are each independently a methyl group.

According to an exemplary embodiment of the present specification, in Chemical Formula 13, L18 is a substituted or unsubstituted arylene group.

According to an exemplary embodiment of the present specification, in Chemical Formula 13, L18 is an arylene group.

According to an exemplary embodiment of the present specification, in Chemical Formula 13, L18 is a phenylene group.

According to an exemplary embodiment of the present specification, in Chemical Formula 13, Ar25 and Ar26 are the same as or different from each other, and are each independently a substituted or unsubstituted aryl group.

According to an exemplary embodiment of the present specification, in Chemical Formula 13, Ar25 and Ar26 are the same as or different from each other, and are each independently an aryl group.

According to an exemplary embodiment of the present specification, in Chemical Formula 13, Ar25 and Ar26 are the same as or different from each other, and are each independently a phenyl group; or a biphenyl group.

According to an exemplary embodiment of the present specification, the P-type host is selected from the following compounds.

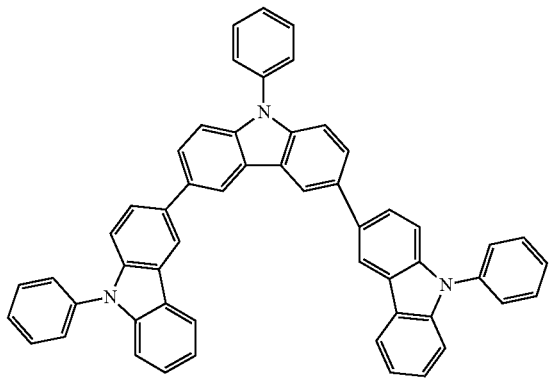
1-2

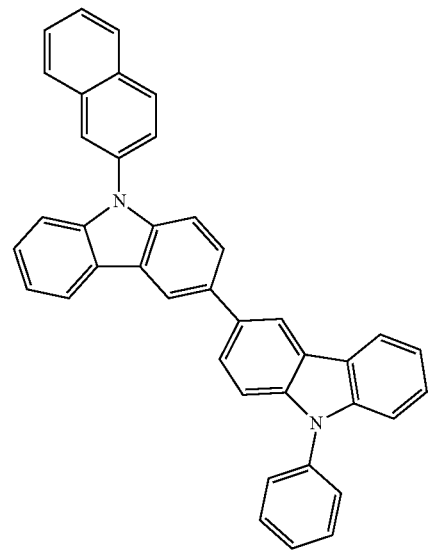
1-3

1-4

1-5

1-6

1-7

1-8
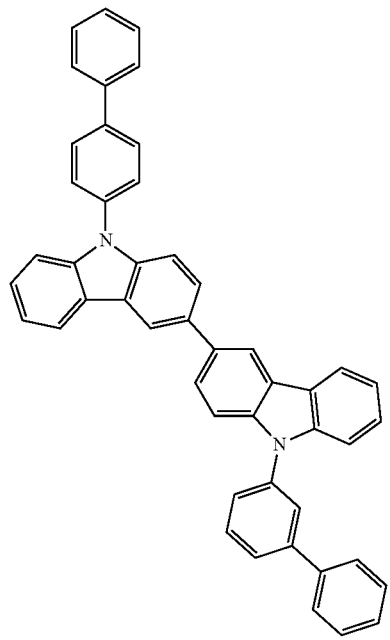
1-9
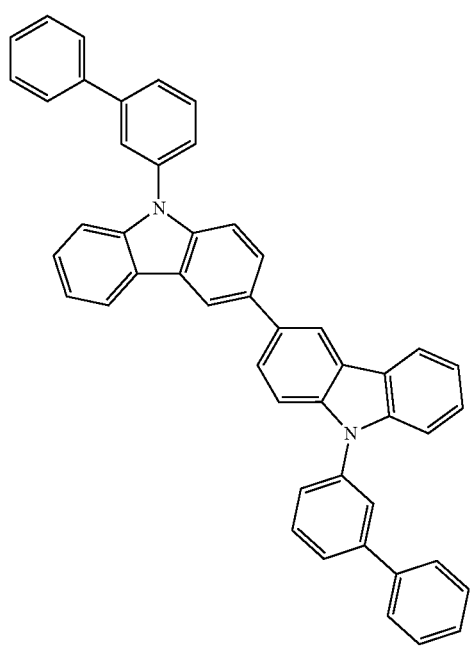
1-10
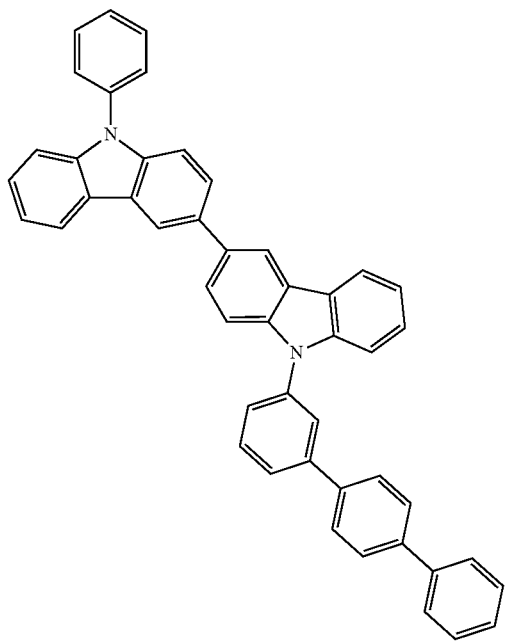
1-11
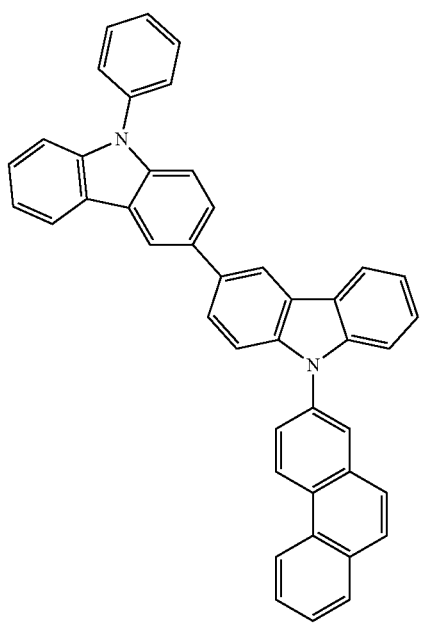

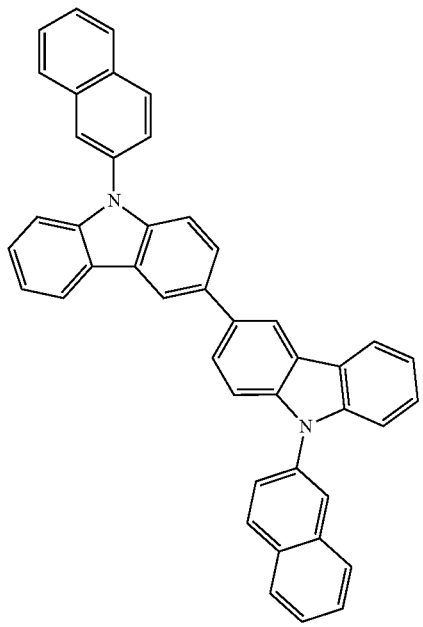
1-12
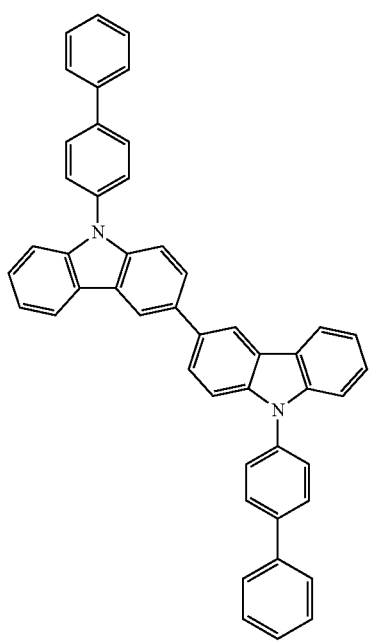
1-13
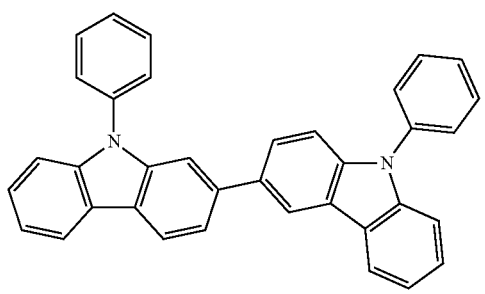
1-14
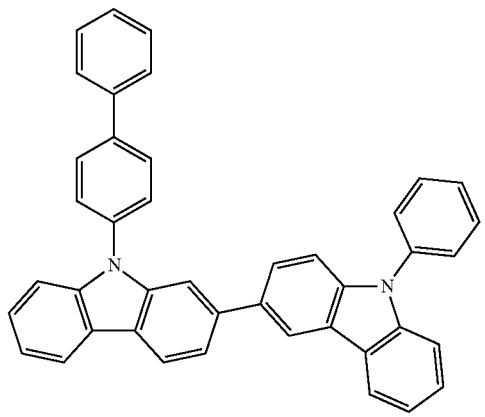
1-15
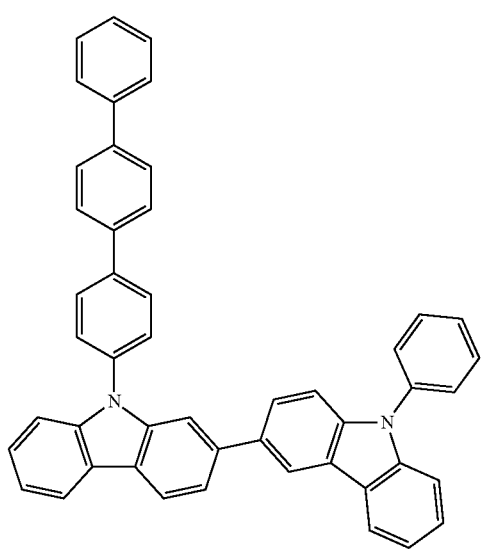
1-16
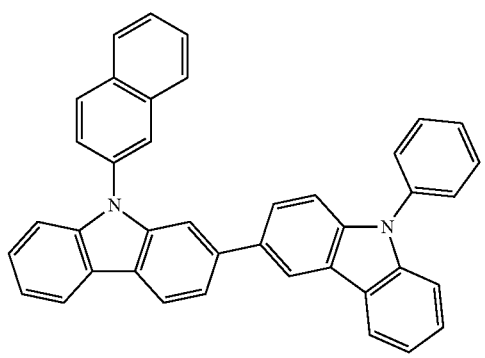
1-17

1-18
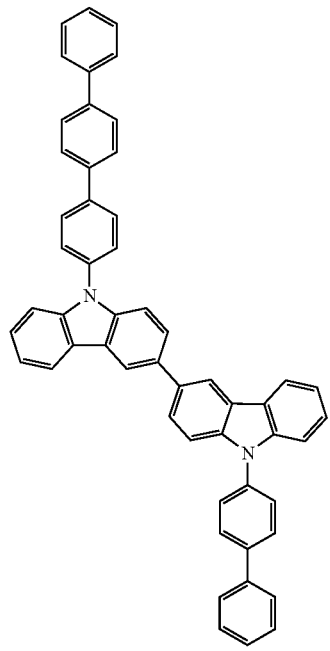
1-19
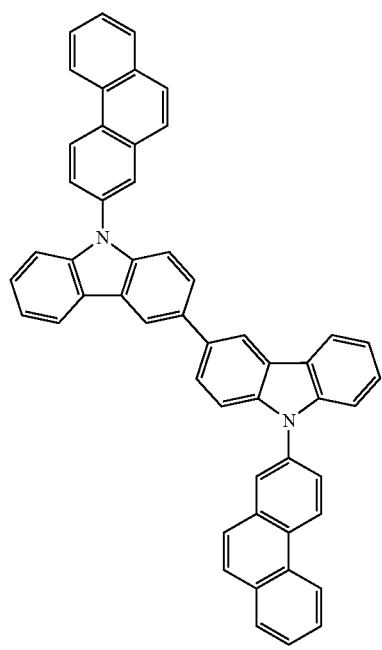
1-20
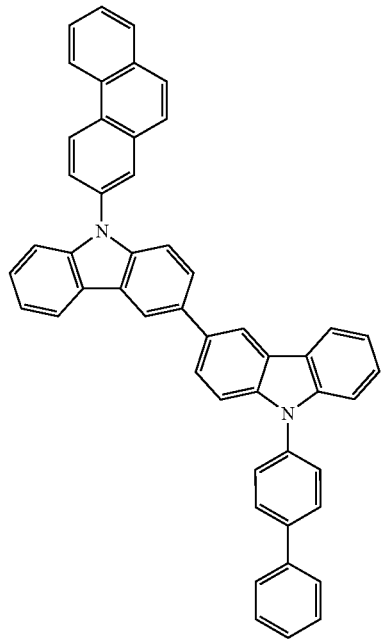
1-21
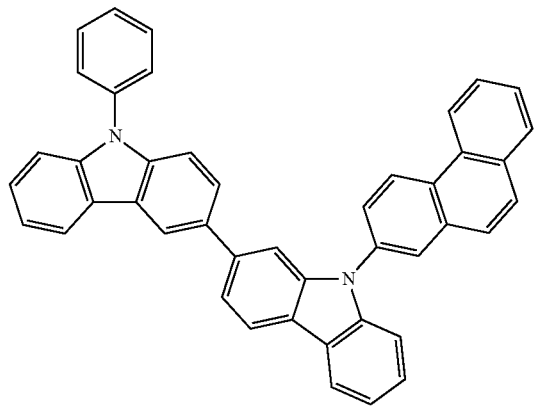
1-22
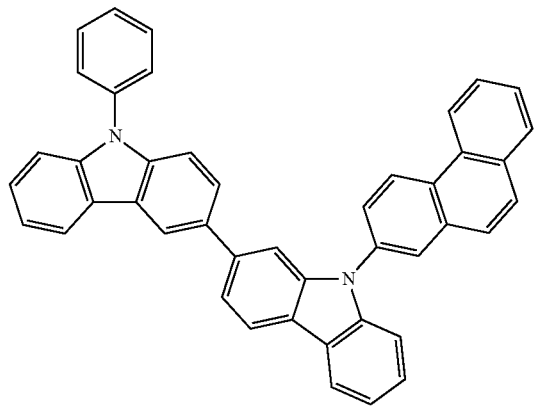

1-23
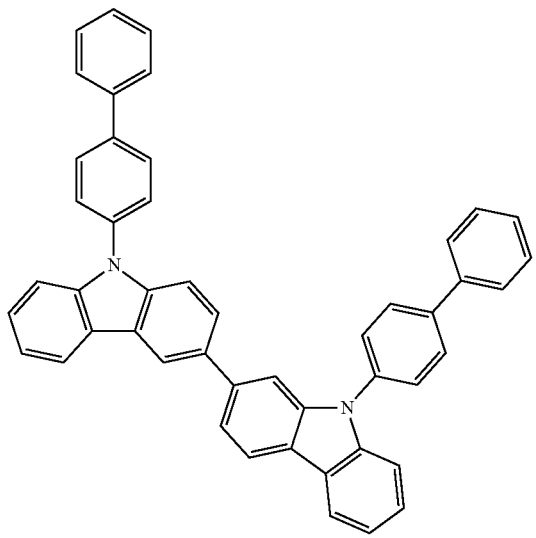
1-24
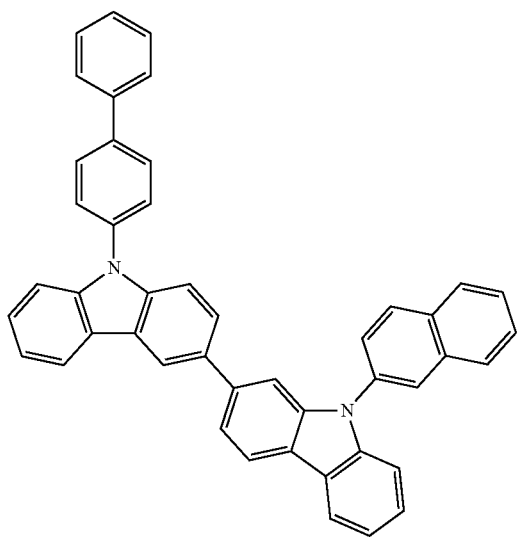
1-25
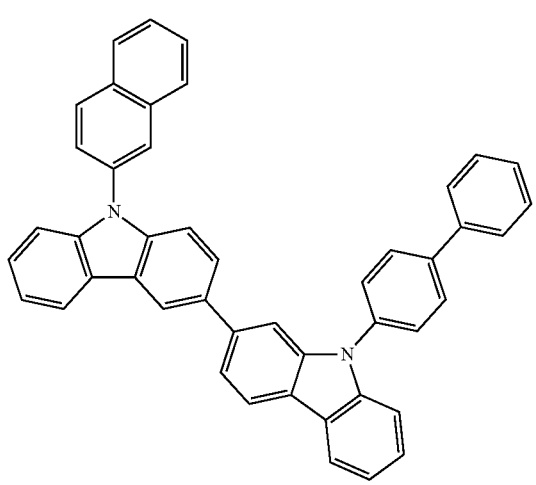
1-26
1-27
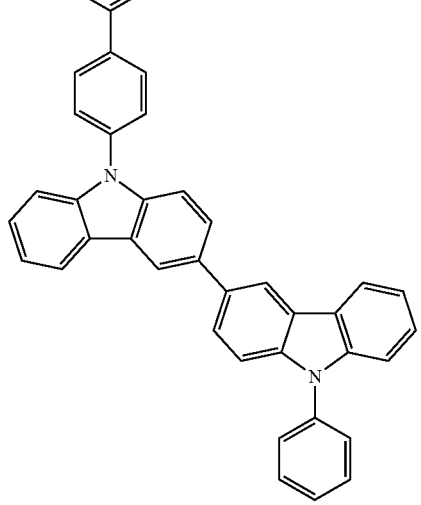
2-1
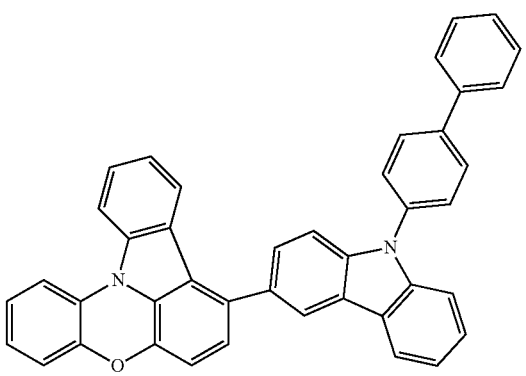

2-2
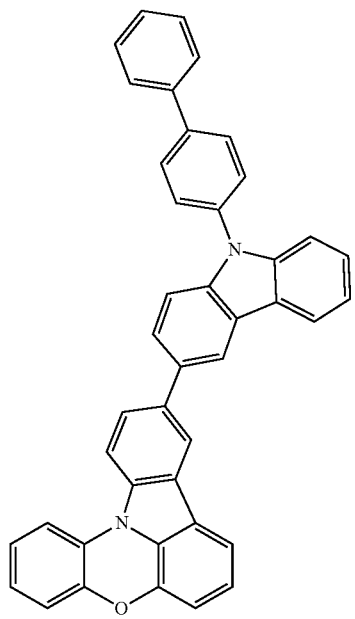
3-1
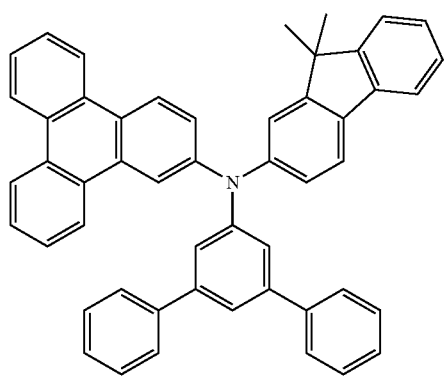
3-2
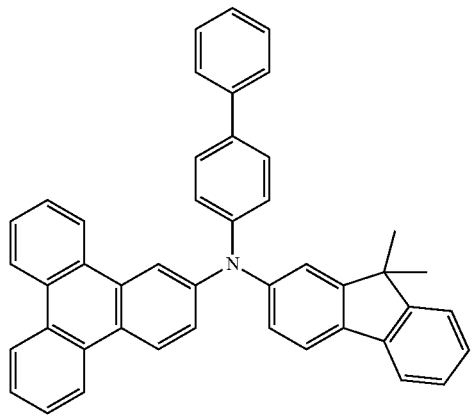
3-3
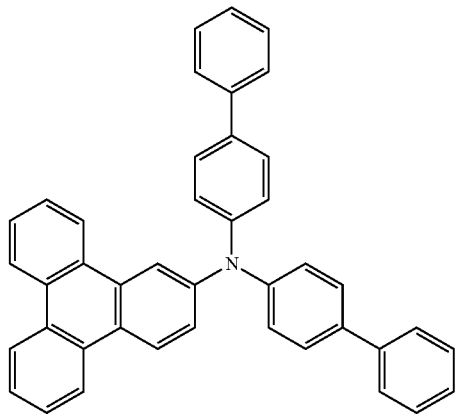
4-1
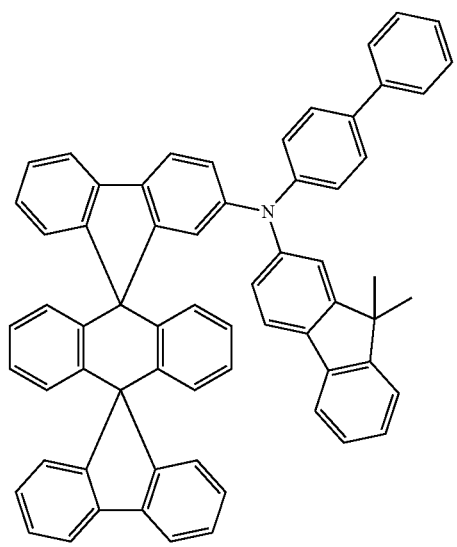
4-2
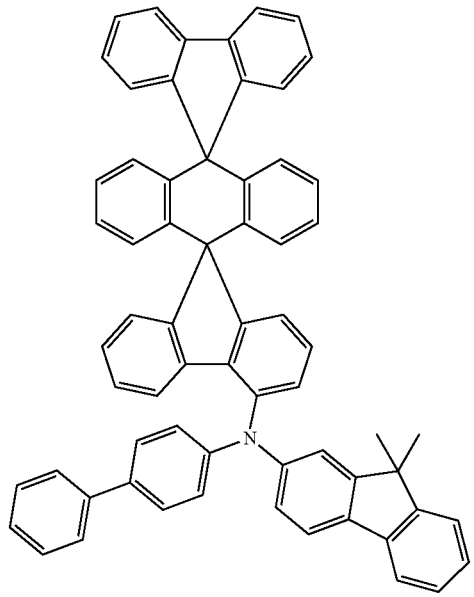

4-3
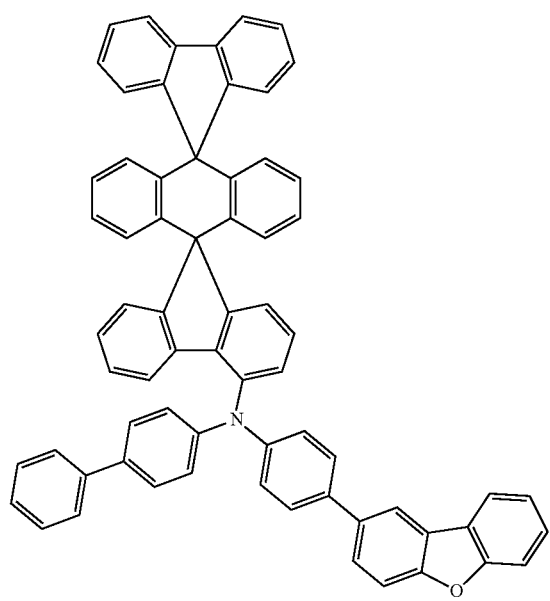
4-4
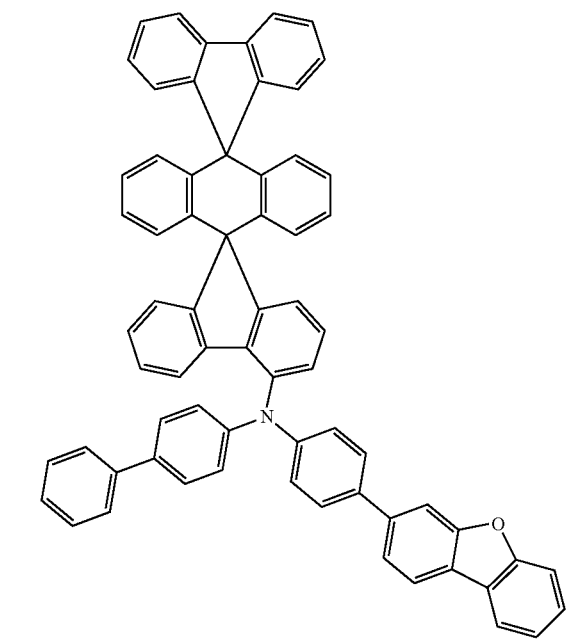
4-5
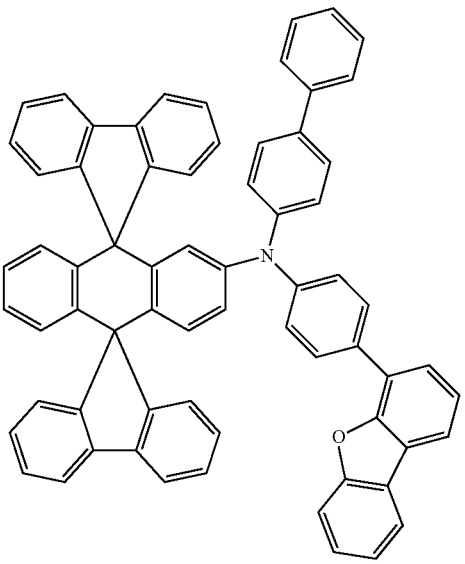
5-1
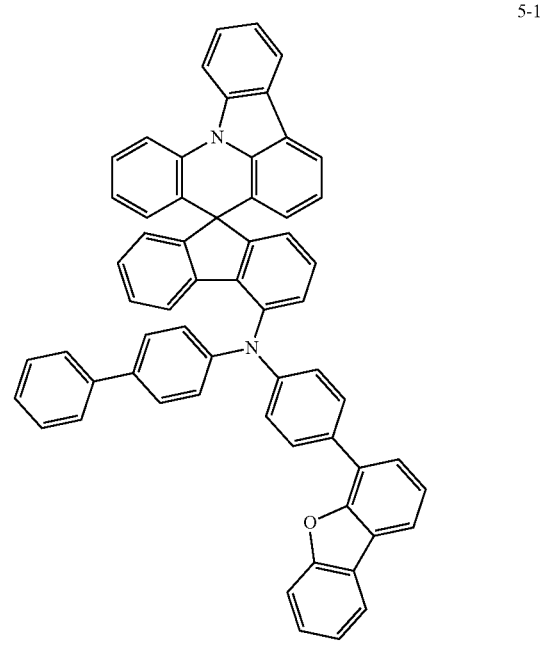
6-1
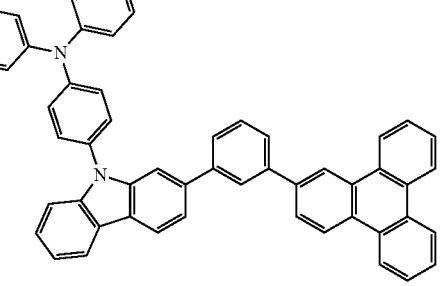

7-1
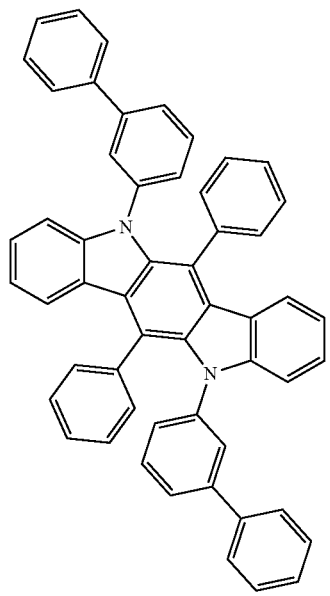
8-1
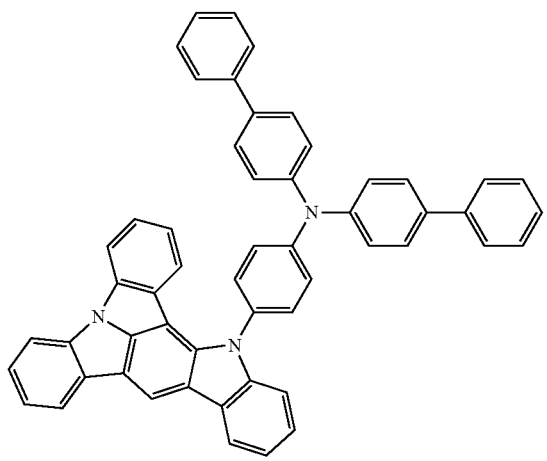
9-1
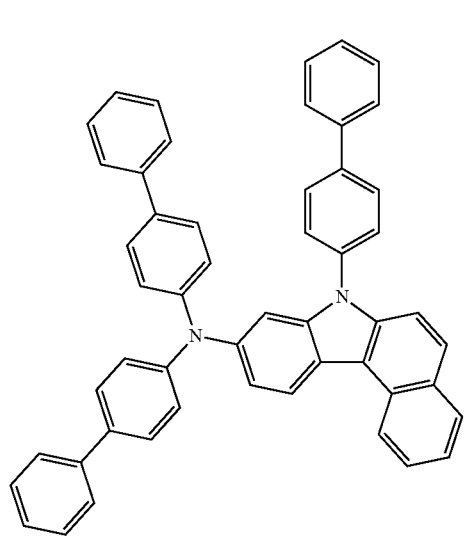
9-2
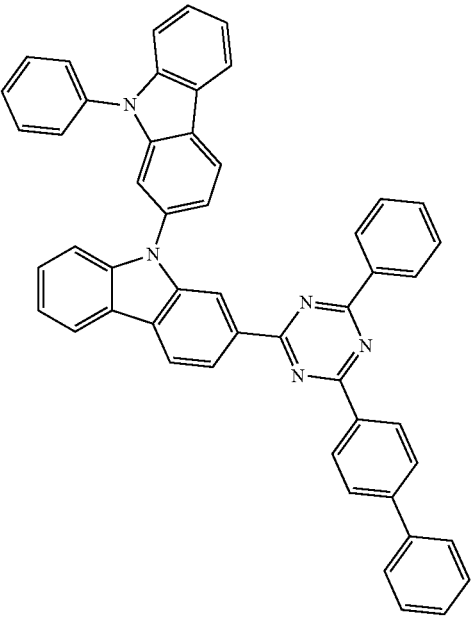
According to an exemplary embodiment of the present specification, the N-type host is selected from the following compounds.
10-1

10-2
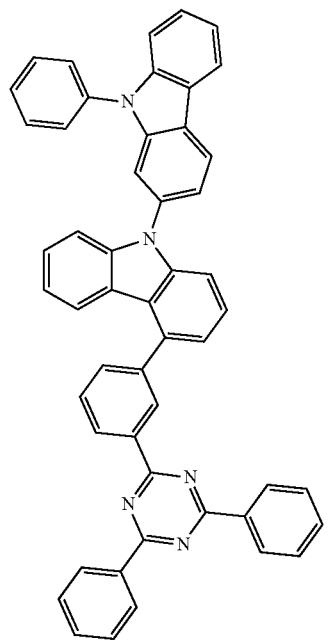
10-3
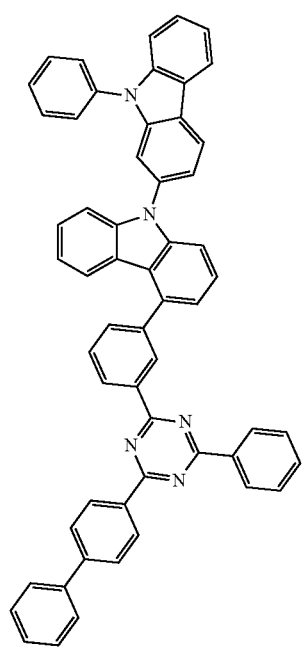
10-4
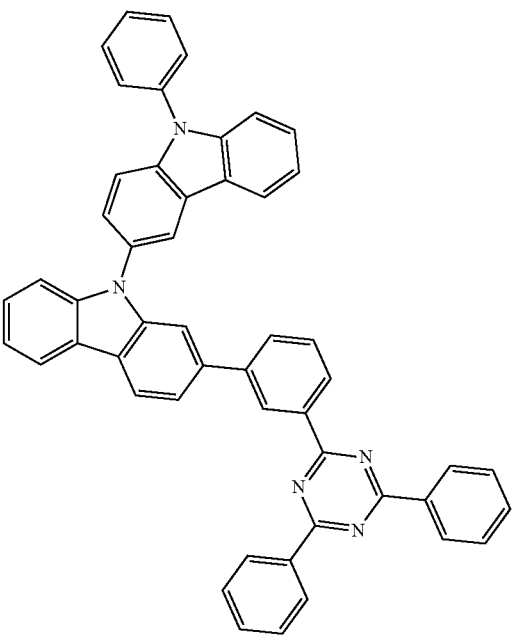
10-5
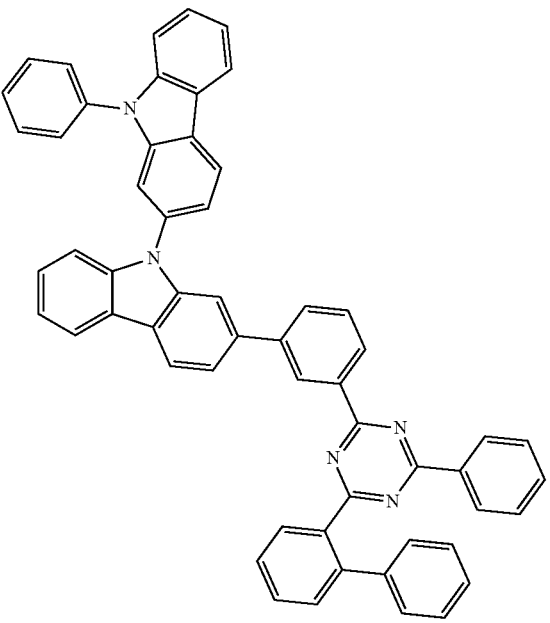

10-6
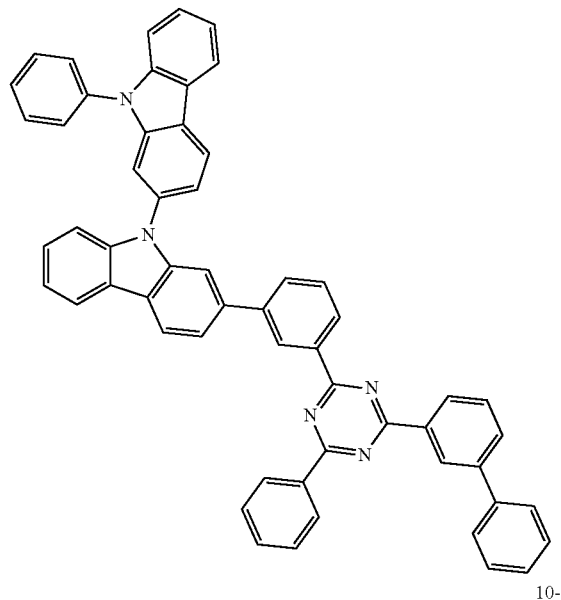
10-7
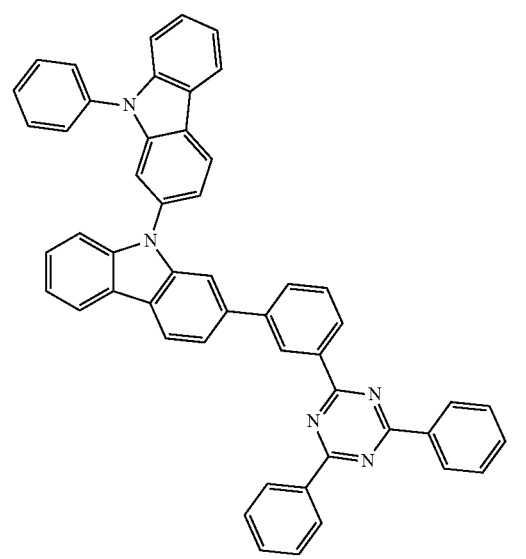
11-1
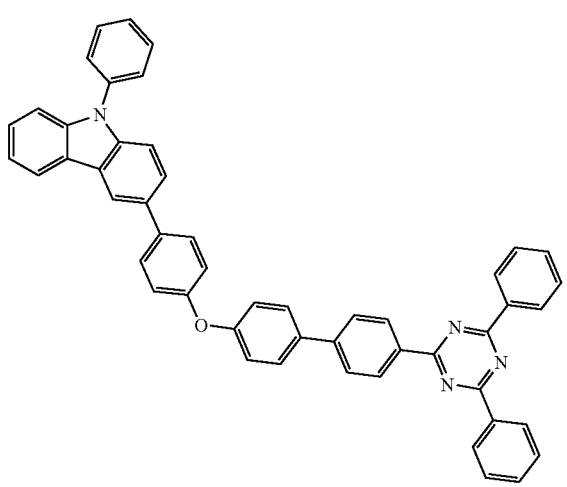
11-2
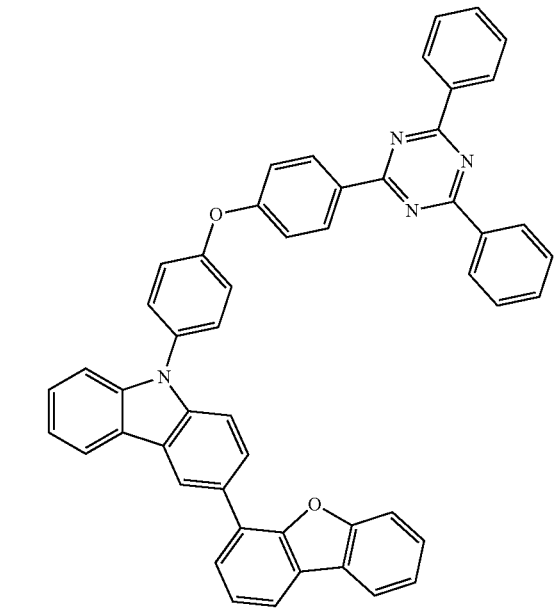
11-3

11-4
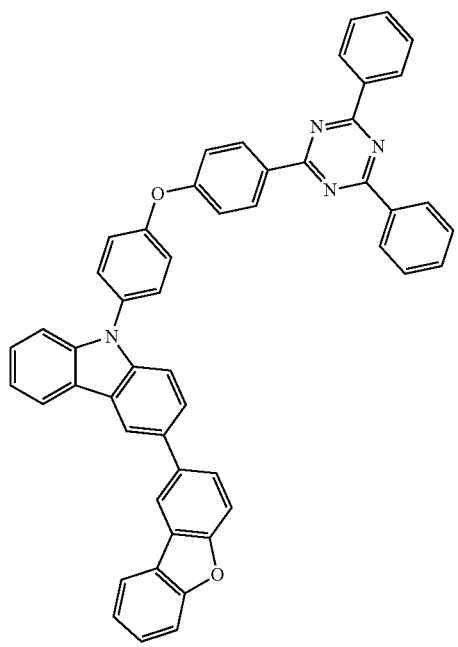
11-5
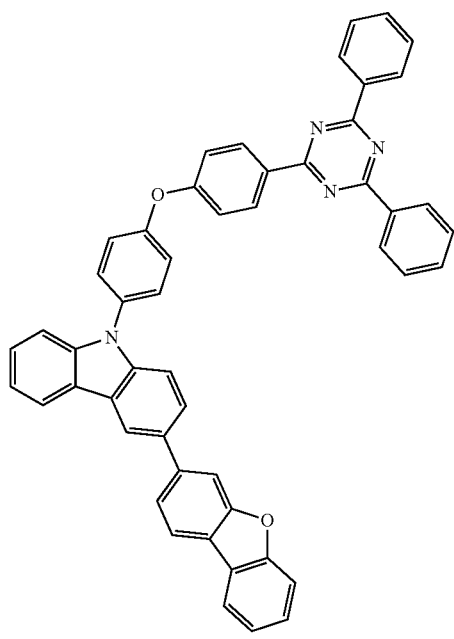
12-1
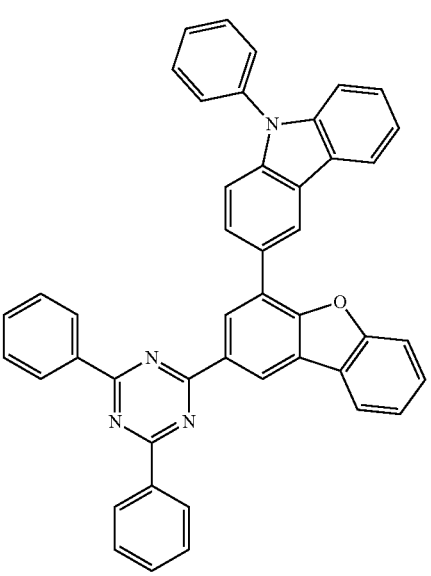
13-1
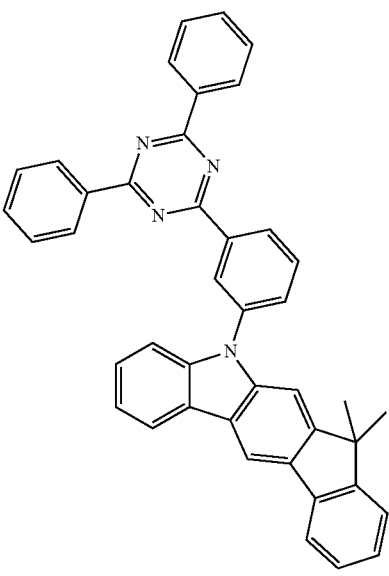

13-2

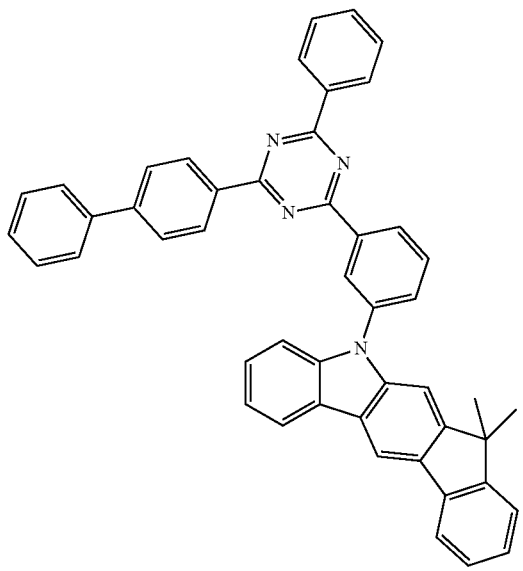

The organic light emitting device of the present specification includes a light emitting layer disposed between the anode and the cathode, and may be manufactured by the materials and methods known in the art, except that the light emitting layer includes: a host including a P-type host and an N-type host which produce an exciplex; and a phosphorescent dopant, the P-type host is any one or more selected from the compounds represented by Chemical Formulae 1 to 9, and the N-type host is any one or more selected from the compounds represented by Chemical Formulae 10 to 13.

Further, according to an exemplary embodiment of the present specification, the materials known in the art may be used as the phosphorescent dopant.

For example, the organic light emitting device of the present specification may be manufactured by sequentially stacking an anode, a light emitting layer, and a cathode on a substrate. In this case, the organic light emitting device may be manufactured by depositing a metal or a metal oxide having conductivity, or an alloy thereof on a substrate to form an anode, forming a hole injection layer, a hole transporting layer, an electron blocking layer, a light emitting layer, an electron transporting layer, and an electron injection layer thereon, and then depositing a material, which may be used as a cathode, thereon, by using a physical vapor deposition (PVD) method such as sputtering or e-beam evaporation. In addition to the method described above, an organic light emitting device may be made by sequentially depositing a cathode material, an electron injection layer, an electron transporting layer, a light emitting layer, an electron blocking layer, a hole transporting layer, a hole injection layer, and an anode material on a substrate.

For example, the structure of the organic light emitting device of the present specification may have a structure as illustrated in FIG. 1, but is not limited thereto.

FIG. 1 exemplifies the structure of an organic light emitting device in which an anode 2, a light emitting layer 3, and a cathode 4 are sequentially stacked on a substrate 1.

FIG. 1 is an exemplified structure of the organic light emitting device according to an exemplary embodiment of the present specification, and may further include one or more selected from the group consisting of an electron injection layer, an electron transporting layer, a hole injection layer, a hole transporting layer, and an electron blocking layer between the anode and the cathode.

The substrate may be a glass substrate or a transparent plastic substrate having excellent transparency, surface smoothness, ease of handling, and waterproofing properties, but is not limited thereto, and the substrate is not limited as long as the substrate is typically used in the organic light emitting device.

As the anode material, materials having a high work function are usually preferred so as to facilitate the injection of holes into an organic material layer.

Specific examples of the anode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the cathode material, materials having a low work function are usually preferred so as to facilitate the injection of electrons into an organic material layer. Specific examples of the cathode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or LiO$_2$/Al, and the like, but are not limited thereto.

The hole injection layer is a layer which injects holes from an electrode, and a hole injection material is preferably a compound which has a capability of transporting holes and thus has an effect of injecting holes at a anode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the anode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a anode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is a material which may emit light in a visible light region by accepting and combining holes and electrons from a hole transporting layer and an electron transporting layer, respectively, and is preferably a material having high quantum efficiency for fluorescence or phosphorescence. Specific examples thereof include: an 8-hydroxy-quinoline aluminum complex ($Alq_3$); carbazole-based compounds; dimerized styryl compounds; Bis(8-hydroxy-2-methylquinoline)-(4-phenylphenoxy)aluminum (BAlq); 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a cathode and transfer the electrons to a light emitting layer. Specific examples thereof include: Al complexes of 8-hydroxyquinoline; complexes including $Alq_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a cathode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and a derivative thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato)chlorogallium, bis(2-methyl-8-quinolinato)(o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a cathode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

According to an exemplary embodiment of the present specification, the organic light emitting device may be a flexible organic light emitting device. In this case, the substrate may include a flexible material. Specifically, the substrate may be a glass in the form of a thin film which may be bent, a plastic substrate, or a substrate in the form of a film.

A material for the plastic substrate is not particularly limited, but may be generally a material including a film such as PET, PEN, PEEK, and PI in the form of a single layer or multiple layers.

The present specification provides a display device including the organic light emitting device. The organic light emitting device in the display device may serve as a pixel or a backlight. In addition, as a configuration of the display device, those known in the art may be applied.

The present specification provides a lighting device including the organic light emitting device. In the lighting device, the organic light emitting device serves as a light emitting unit. In addition, as the configurations required for the lighting device, those known in the art may be applied.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

The compounds of Chemical Formulae 1 to 13 may be prepared by the preparation methods known in the art.

Examples 1-1 to 1-42

Heat is applied to a P-type host and an N-type host described in the following Table 1 at a mixture ratio of 5:5 in a vacuum state of $10^{-7}$ Torr or less on a transparent quartz substrate, thereby simultaneously depositing the P-type host and the N-type host to have a film thickness of 100 nm or more on the quartz substrate at a deposition rate of 1 Å/sec. A photoluminescence spectrum in the following Table 1 was obtained by measuring the film by means of a general photoluminescence measuring apparatus.

Comparative Examples 1-1 to 1-45

Heat is applied to each of a P-type host and an N-type host described in the following Table 1 and Comparative Example Compounds A and B in a vacuum state of $10^{-7}$ Torr or less on a transparent quartz substrate, thereby depositing the P-type host and the N-type host to have a film thickness of 100 nm or more on the quartz substrate at a deposition rate of 1 Å/sec. A photoluminescence spectrum in the following Table 1 was obtained by measuring the film by means of a general photoluminescence measuring apparatus.

Comparative Example Compound A

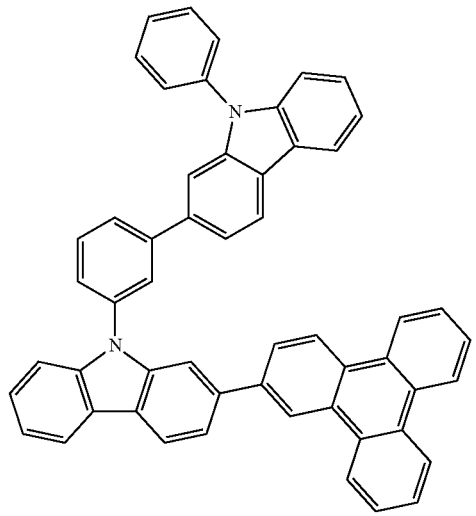

Comparative Example Compound B

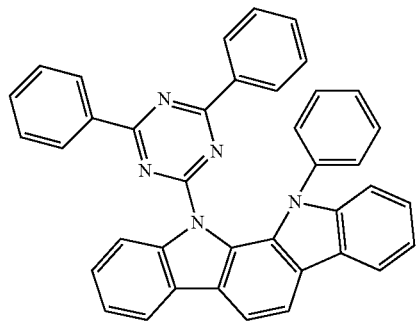

TABLE 1

| | Compound | PL peak (eV) | | Compound | PL peak (eV) |
|---|---|---|---|---|---|
| Comparative Example 1-1 | Compound 1-1 | 3.01 | Example 1-1 | Compound 1-1 + Compound 10-7 | 2.49 |
| Comparative Example 1-2 | Compound 1-2 | 2.95 | Example 1-2 | Compound 1-2 + Compound 10-7 | 2.48 |
| Comparative Example 1-3 | Compound 1-3 | 3.00 | Example 1-3 | Compound 1-3 + Compound 13-1 | 2.54 |
| Comparative Example 1-4 | Compound 1-4 | 2.99 | Example 1-4 | Compound 1-4 + Compound 10-7 | 2.56 |
| Comparative Example 1-5 | Compound 1-5 | 2.97 | Example 1-5 | Compound 1-5 + Compound 13-1 | 2.55 |
| Comparative Example 1-6 | Compound 1-6 | 2.98 | Example 1-6 | Compound 1-6 + Compound 13-1 | 2.56 |
| Comparative Example 1-7 | Compound 1-7 | 2.98 | Example 1-7 | Compound 1-7 + Compound 13-1 | 2.51 |

TABLE 1-continued

|  | Compound | PL peak (eV) |  | Compound | PL peak (eV) |
|---|---|---|---|---|---|
| Comparative Example 1-8 | Compound 1-8 | 3.00 | Example 1-8 | Compound 1-8 + Compound 13-1 | 2.47 |
| Comparative Example 1-9 | Compound 1-9 | 3.00 | Example 1-9 | Compound 1-9 + Compound 13-1 | 2.49 |
| Comparative Example 1-10 | Compound 1-10 | 3.00 | Example 1-10 | Compound 1-10 + Compound 13-1 | 2.55 |
| Comparative Example 1-11 | Compound 1-11 | 3.00 | Example 1-11 | Compound 1-11 + Compound 13-1 | 2.50 |
| Comparative Example 1-12 | Compound 1-12 | 2.93 | Example 1-12 | Compound 1-12 + Compound 13-1 | 2.44 |
| Comparative Example 1-13 | Compound 2-1 | 2.93 | Example 1-13 | Compound 2-1 + Compound 13-1 | 2.39 |
| Comparative Example 1-14 | Compound 2-2 | 2.88 | Example 1-14 | Compound 2-2 + Compound 13-1 | 2.39 |
| Comparative Example 1-15 | Compound 3-1 | 2.92 | Example 1-15 | Compound 3-1 + Compound 13-1 | 2.52 |
| Comparative Example 1-16 | Compound 3-2 | 2.96 | Example 1-16 | Compound 3-2 + Compound 13-1 | 2.41 |
| Comparative Example 1-17 | Compound 4-1 | 3.01 | Example 1-17 | Compound 4-1 + Compound 13-1 | 2.37 |
| Comparative Example 1-18 | Compound 4-2 | 3.00 | Example 1-18 | Compound 4-2 + Compound 13-1 | 2.55 |
| Comparative Example 1-19 | Compound 4-3 | 3.02 | Example 1-19 | Compound 4-3 + Compound 13-1 | 2.58 |
| Comparative Example 1-20 | Compound 4-4 | 2.97 | Example 1-20 | Compound 4-4 + Compound 13-1 | 2.61 |
| Comparative Example 1-21 | Compound 4-5 | 2.97 | Example 1-21 | Compound 4-5 + Compound 13-1 | 2.42 |
| Comparative Example 1-22 | Compound 5-1 | 3.01 | Example 1-22 | Compound 5-1 + Compound 13-1 | 2.61 |
| Comparative Example 1-23 | Compound 6-1 | 2.97 | Example 1-23 | Compound 6-1 + Compound 13-1 | 2.41 |
| Comparative Example 1-24 | Compound 7-1 | 2.91 | Example 1-24 | Compound 7-1 + Compound 13-1 | 2.44 |
| Comparative Example 1-25 | Compound 8-1 | 2.97 | Example 1-25 | Compound 8-1 + Compound 13-1 | 2.55 |
| Comparative Example 1-26 | Compound 9-1 | 2.90 | Example 1-26 | Compound 9-1 + Compound 13-1 | 2.32 |

TABLE 1-continued

|  | Compound | PL peak (eV) |  | Compound | PL peak (eV) |
|---|---|---|---|---|---|
| Comparative Example 1-27 | Compound 9-2 | 2.87 | Example 1-27 | Compound 9-2 + Compound 13-1 | 2.28 |
| Comparative Example 1-28 | Compound 10-1 | 2.72 | Example 1-28 | Compound 1-1 + Compound 10-1 | 2.60 |
| Comparative Example 1-29 | Compound 10-2 | 2.86 | Example 1-29 | Compound 1-1 + Compound 10-2 | 2.52 |
| Comparative Example 1-30 | Compound 10-3 | 2.83 | Example 1-30 | Compound 1-1 + Compound 10-3 | 2.51 |
| Comparative Example 1-31 | Compound 10-4 | 2.74 | Example 1-31 | Compound 1-1 + Compound 10-4 | 2.53 |
| Comparative Example 1-32 | Compound 10-5 | 2.84 | Example 1-32 | Compound 1-1 + Compound 10-5 | 2.64 |
| Comparative Example 1-33 | Compound 10-6 | 2.83 | Example 1-33 | Compound 1-1 + Compound 10-6 | 2.51 |
| Comparative Example 1-34 | Compound 10-7 | 2.85 | Example 1-34 | Compound 1-1 + Compound 11-1 | 2.53 |
| Comparative Example 1-35 | Compound 11-1 | 2.73 | Example 1-35 | Compound 1-1 + Compound 11-2 | 2.57 |
| Comparative Example 1-36 | Compound 11-2 | 2.85 | Example 1-36 | Compound 1-1 + Compound 11-3 | 2.54 |
| Comparative Example 1-37 | Compound 11-3 | 2.84 | Example 1-37 | Compound 1-1 + Compound 11-4 | 2.54 |
| Comparative Example 1-38 | Compound 11-4 | 2.76 | Example 1-38 | Compound 1-1 + Compound 11-5 | 2.58 |
| Comparative Example 1-39 | Compound 11-5 | 2.80 | Example 1-39 | Compound 1-1 + Compound 12-1 | 2.67 |
| Comparative Example 1-40 | Compound 12-1 | 2.83 | Example 1-40 | Compound 1-1 + Compound 13-1 | 2.05 |
| Comparative Example 1-41 | Compound 13-1 | 2.58 | Example 1-41 | Compound 1-2 + Compound 13-1 | 2.45 |
| Comparative Example 1-42 | Compound 13-2 | 2.63 | Example 1-42 | Compound 1-4 + Compound 13-1 | 2.46 |
| Comparative Example 1-43 | Comparative Example Compound A | 3.06 | Comparative Example 1-44 | Comparative Example Compound B | 2.41 |
| Comparative Example 1-45 | Comparative Example Compound A + Comparative Example Compound B | 2.45 |  |  |  |

In Table 1, it can be seen that a photoluminescence peak of the host including the P-type host and the N-type host, which produce an exciplex, according to an exemplary embodiment, has lower photon energy than a photon energy of each photoluminescence peak of the P-type host and the N-type host.

Figure 2:
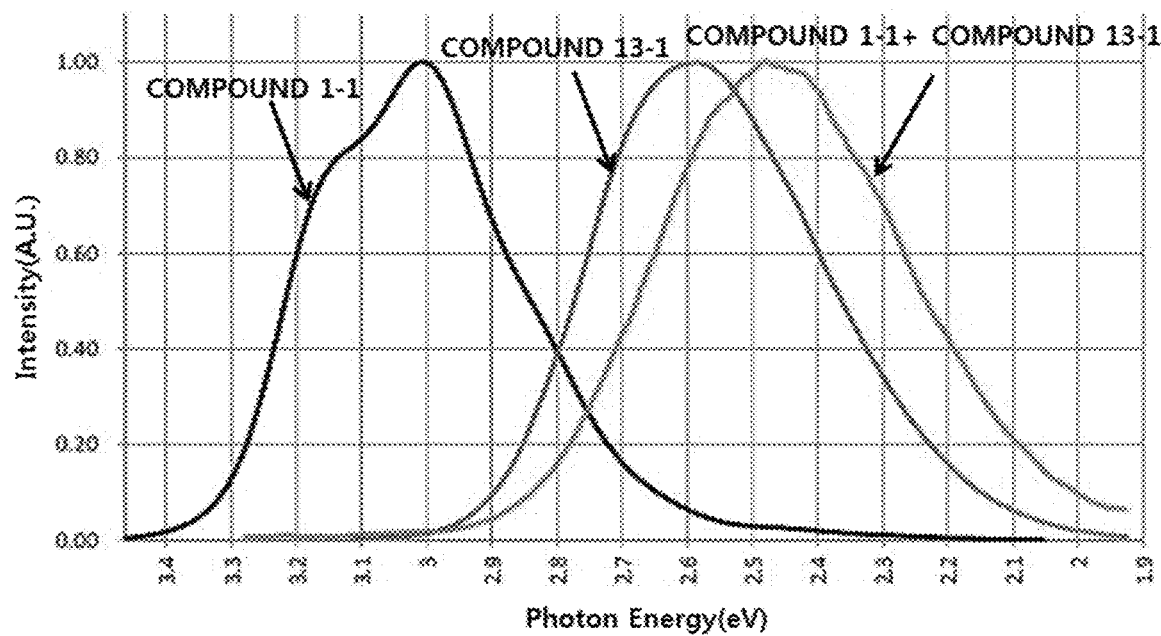
FIG. 2 is a view illustrating the photoluminescence of Comparative Example 1-1, Comparative Example 1-41, and Example 1-40.

Further, FIG. 2 is a view illustrating the photoluminescence of Comparative Example 1-1, Comparative Example 1-41, and Example 1-40.

Figure 3:
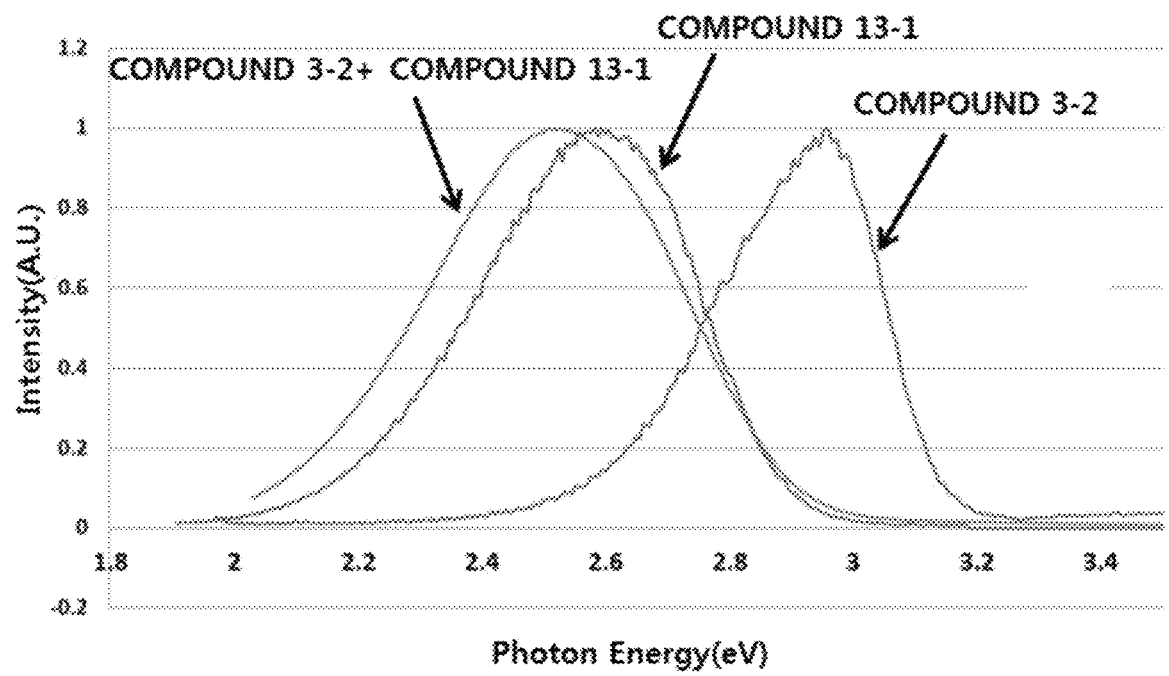
FIG. 3 is a view illustrating the photoluminescence of Comparative Example 1-16, Comparative Example 1-41, and Example 1-16.
Figure 4:
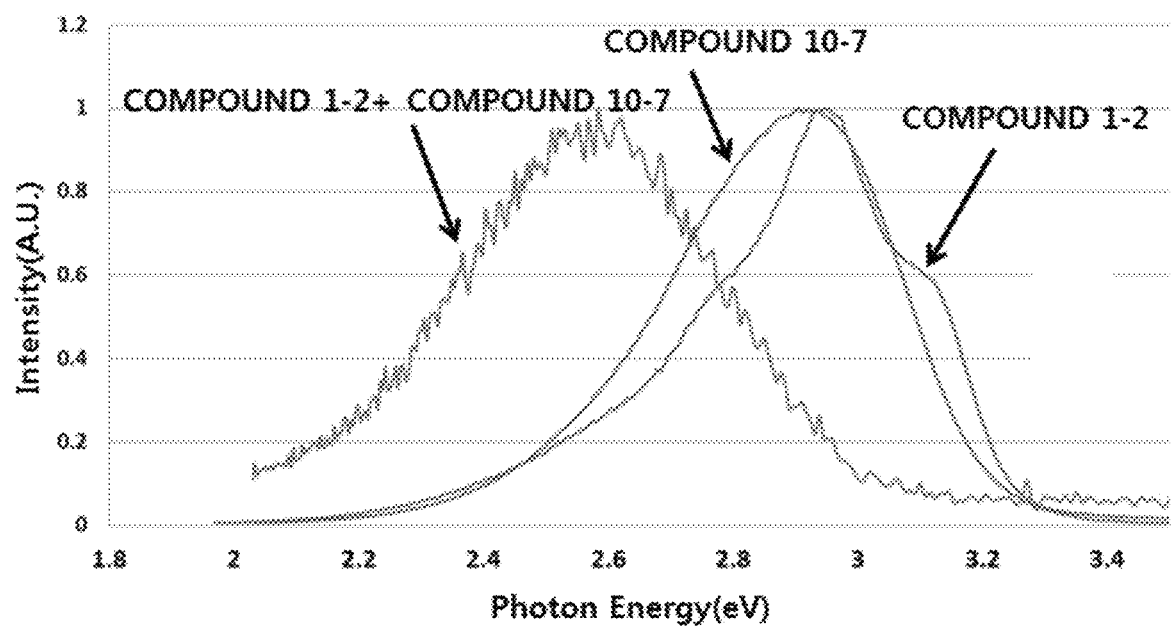
FIG. 4 is a view illustrating the photoluminescence of Comparative Example 1-2, Comparative Example 1-34, and Example 1-2.

FIG. 3 is a view illustrating the photoluminescence of Comparative Example 1-16, Comparative Example 1-41, and Example 1-16, and FIG. 4 is a view illustrating the photoluminescence of Comparative Example 1-2, Comparative Example 1-34, and Example 1-2.

Figure 5:
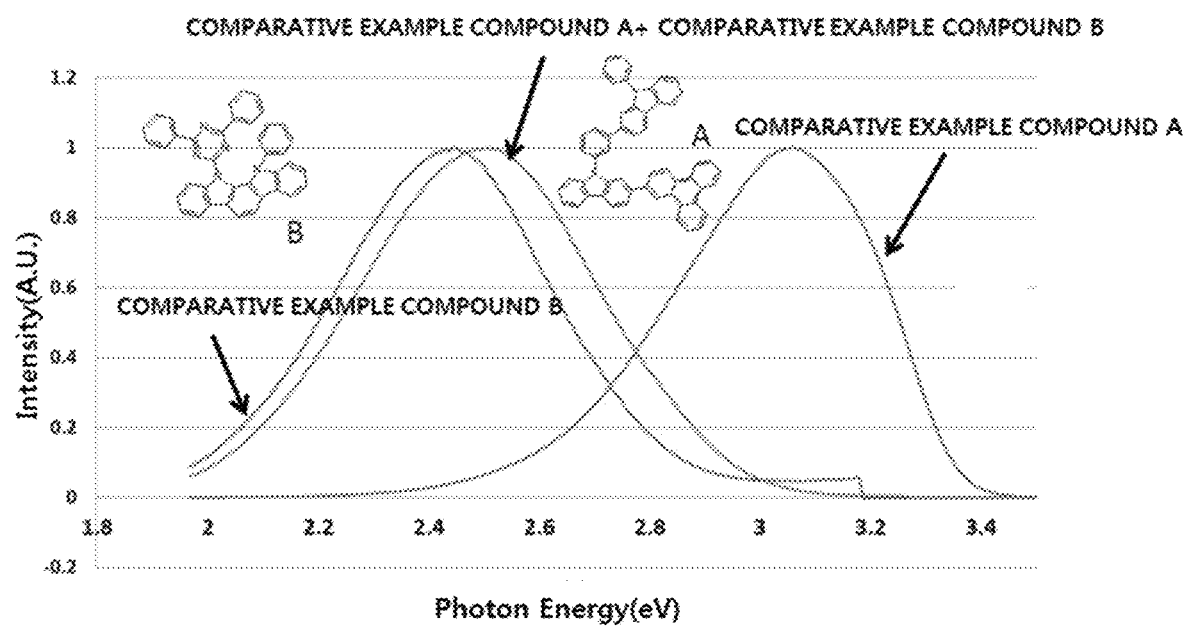
FIG. 5 is a view illustrating the photoluminescence of Comparative Example 1-43, Comparative Example 1-44, and Comparative Example 1-45.

FIG. 5 is a view illustrating the photoluminescence of Comparative Example 1-43, Comparative Example 1-44, and Comparative Example 1-45.

Since the energy of the photoluminescence peak of Comparative Example Compound B in Comparative Example 1-44 is higher than the photon energy of the photoluminescence peak in which Comparative Example Compound A and Comparative Example Compound B in Comparative Example 1-45 are used, it can be seen that the host in which Comparative Example Compound A and Comparative Example Compound B are used does not produce the exciplex.

Examples 2-1 to 2-42

A substrate including a transparent electrode (indium tin oxide) as a hole injection electrode on a glass substrate having a thickness of 100 nm was subjected to an oxygen plasma treatment at 80 w under a pressure of 30 mtorr for 30 seconds. Heat was added thereon in a vacuum state, thereby depositing [cp1] to have a thickness of 5 nm. [cp2] being NPB (N,N'-Bis-(1-naphthalenyl)-N,N'-bis-phenyl-(1,1'-biphenyl)-4,4'-diamine) as a hole injection layer was deposited to have a thickness of 25 nm thereon. [cp3] was deposited to have a thickness of 5 nm as an electron blocking layer thereon. A P-type host and an N-type host described in the following Table 2 were co-deposited at 5:5 as hosts of a light emitting layer, the hosts were doped with 10% [cp4] being a phosphorescent light emitting dopant to have a thickness of 40 nm, and subsequently, [cp5] was deposited thereon as an electron transporting layer to have a thickness of 25 nm, and 2% Li was doped and deposited to have a thickness of 10 nm on [cp6] as an electron injection layer. Aluminum (Al) as an electron injection electrode was deposited to have a thickness of 150 nm thereon, thereby manufacturing an organic light emitting device.

[cp1]

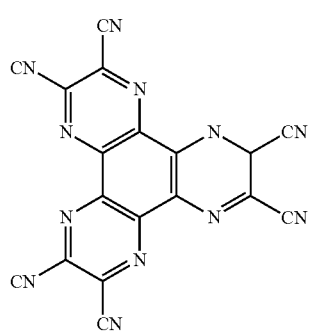

[cp2]

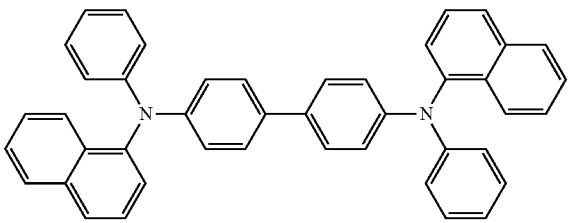

[cp3]

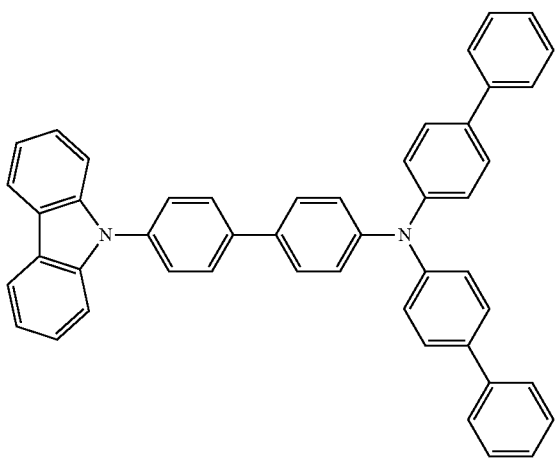

[cp4]

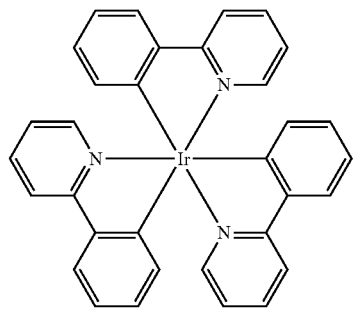

[cp5]

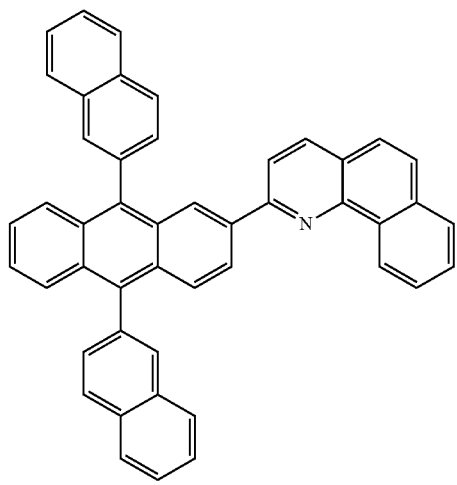

-continued

[cp6]

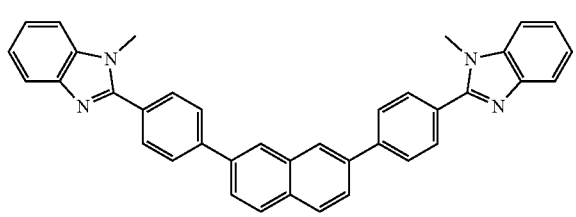

Comparative Examples 2-1 to 2-45

An organic light emitting device was manufactured in the same manner as in Examples 2-1 to 2-42, except that each of a P-type host and an N-type host in the following Table 3 and Comparative Example Compounds A and B were used as hosts of the light emitting layer.

Comparative Example Compound A

Comparative Example Compound B

For the manufactured organic light emitting devices in Examples 2-1 to 2-42 and Comparative Examples 2-1 to 2-45, the efficiencies according to the change in current density at 0.01 mA/cm² to 100 mA/cm² were measured, and the results are shown in the following Tables 2 and 3. As the efficiency in the following Tables 2 and 3, the efficiency at 10 mA/cm was shown.

Figure 6:
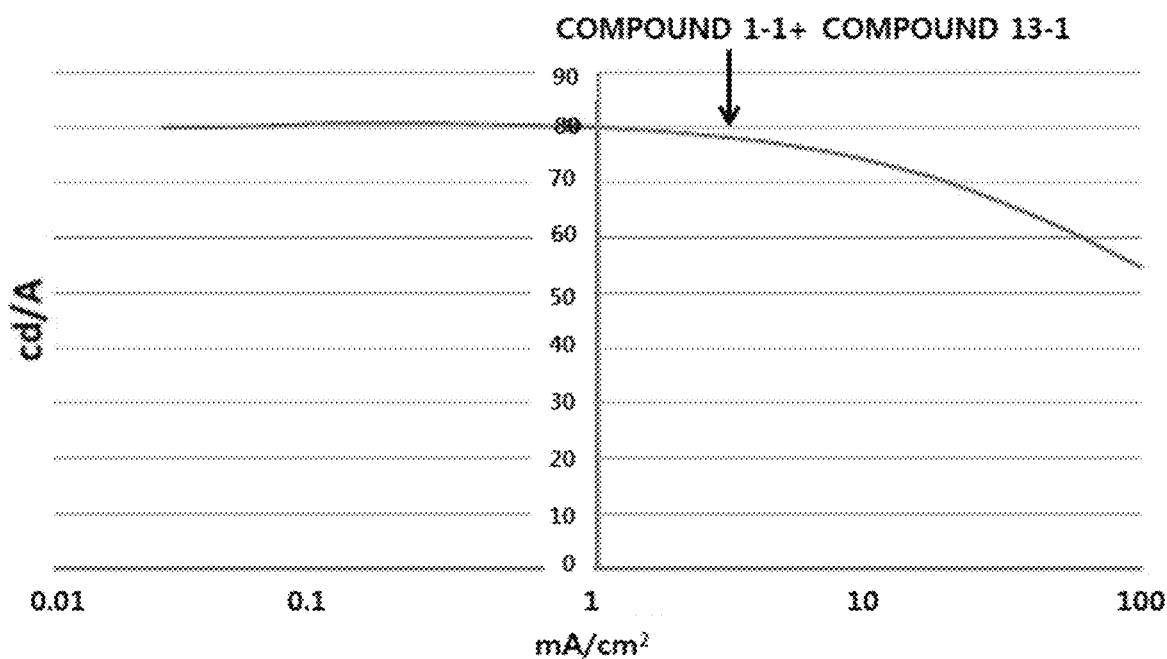
FIG. 6 is a graph illustrating the efficiency of the organic light emitting device of Example 2-40 according to a change in current density.
Figure 7:
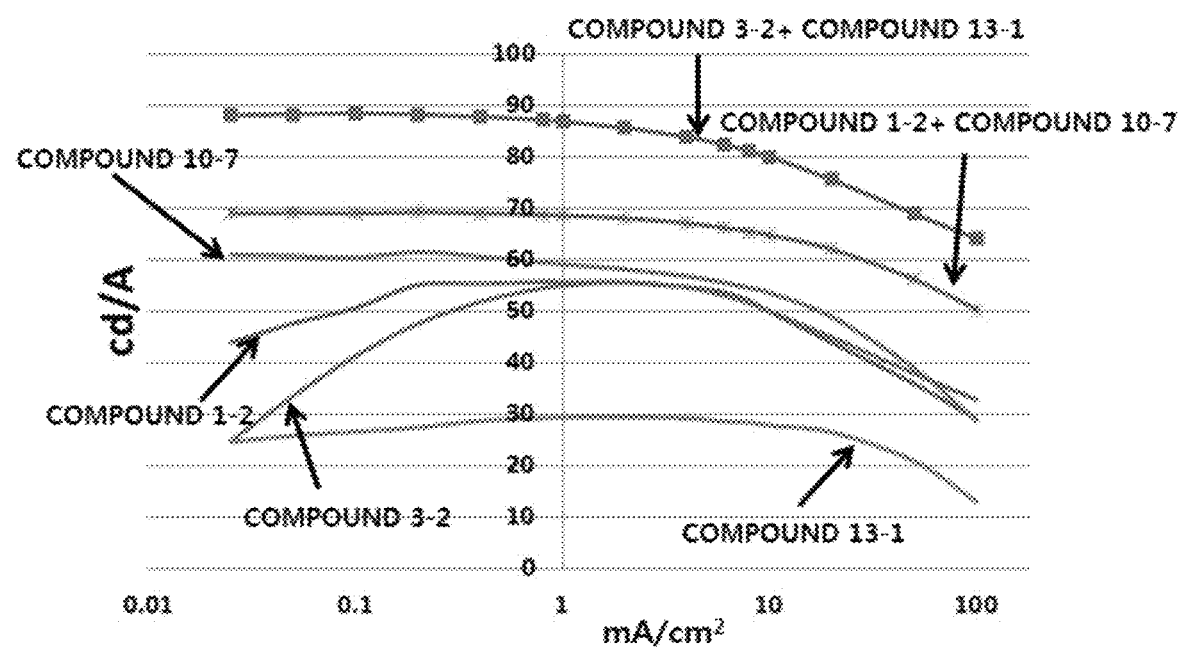
FIG. 7 is a graph illustrating the efficiency of the organic light emitting devices of Comparative Examples 2-2, 2-16, 2-34, and 2-41 and Examples 2-2 and 2-16 according to a change in current density.
Figure 8:
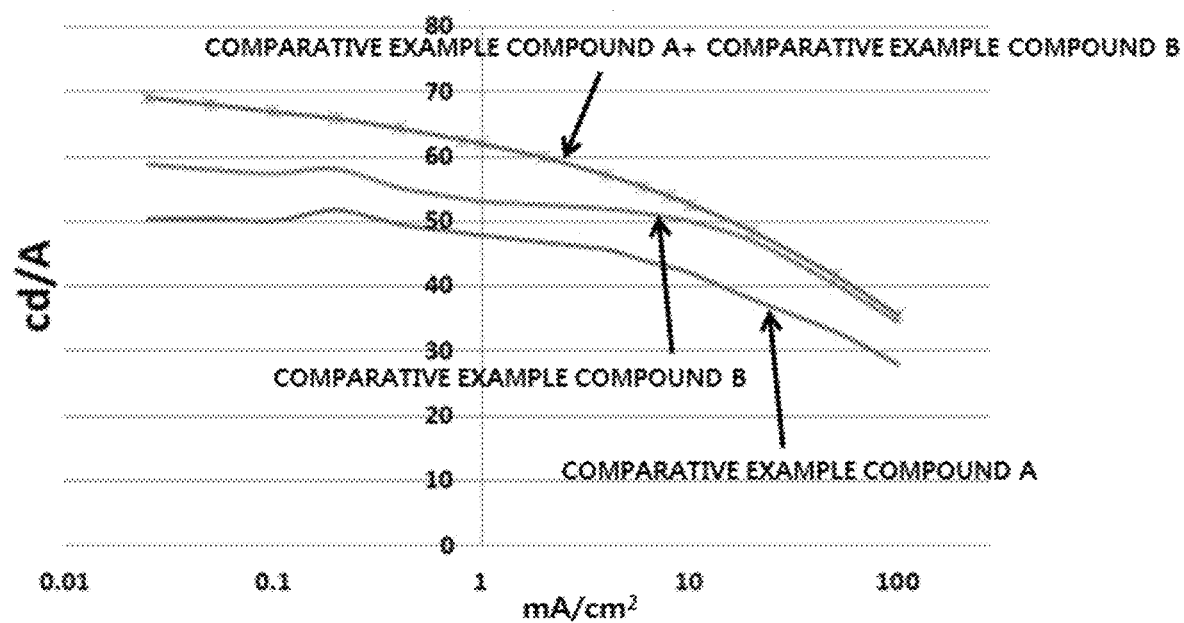
FIG. 8 is a graph illustrating the efficiency of the organic light emitting devices of Comparative Examples 2-43 to 2-45 according to a change in current density.
Figure 9:
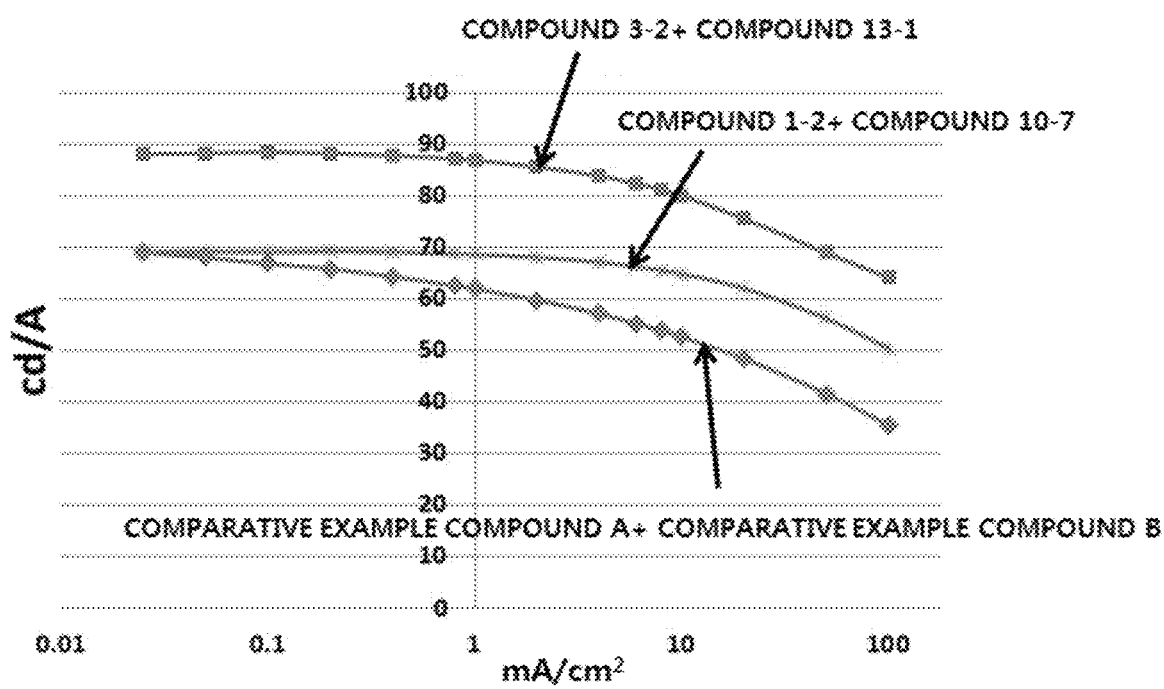
FIG. 9 is a graph illustrating the efficiency of the organic light emitting devices of Examples 2-2 and 2-16 and Comparative Example 2-45 according to a change in current density.

FIG. 6 illustrates the efficiency of the organic light emitting device in Example 2-40 according to the change in current density, FIG. 7 illustrates the efficiencies of the organic light emitting devices in Comparative Examples 2-2, 2-16, 2-34, and 2-41 and Examples 2-2 and 2-16 according to the change in current density, FIG. 8 illustrates the efficiencies of the organic light emitting devices in Comparative Examples 2-43 to 2-45 according to the change in current density, and FIG. 9 illustrates the efficiencies of the organic light emitting devices in Examples 2-2 and 2-6 and Comparative Example 2-45 according to the change in current density.

The efficiency ratio was calculated by the following Equation 1, and according to FIG. 6, in the organic light emitting device in Example 2-40, the highest efficiency was 80.7 cd/A at 0.2 mA/cm² and the lowest efficiency was 54.7 cd/A at 100 mA/cm².

Efficiency ratio=(max·cd/A)/(cd/A(at 100 mA/cm²))  [Equation 1]

The efficiency ratio of the organic light emitting device in Example 2-40 is 1.48 and has a value of 1.6 or less, and the stability of the organic light emitting device is high because the change width in current density according to the current change is small.

Further, in the following Tables 2 and 3, it can be seen that the organic light emitting devices in Comparative Examples 2-1 to 2-42 in which the P-type host and the N-type host are each included as a host, Comparative Example 2-43 in which Comparative Example Compound A is included as a host, Comparative Example 2-44 in which Comparative Example Compound B is included as a host, and Comparative Example 2-45 in which Comparative Example Compounds A and B, which do not produce an exciplex, are included as a host have an efficiency ratio of more than 1.6, but the organic light emitting devices in Examples 2-1 to 2-42 in which the host including the P-type host and the N-type host, which produce the exciplex, according to an exemplary embodiment of the present specification, is used have an efficiency ratio of 1.6 or less, and the stability of the organic light-emitting devices is high because the change width in current density according to the current change is small.

Specifically, the efficiencies and efficiency ratios calculated by Equation 1 in the organic light emitting devices according to FIGS. 7 to 9 are shown in the following Table 4. According to FIGS. 7 to 9 and Table 4, it can be seen that the organic light emitting devices in Examples 2-2 and 2-16 which include the host including the P-type host and the N-type host, which produce the exciplex, according to an exemplary embodiment of the present specification have an efficiency ratio of 1.6 or less, but the organic light emitting devices in Comparative Examples 2-2, 2-16, 2-34, 2-41, and 2-43 to 2-45 which include each of the P-type host and the N-type host, or Comparative Example Compound A or B, which does not produce the exciplex, and Comparative Example Compounds A and B have an efficiency ratio of more than 1.6.

TABLE 2

| | Compound | Driving voltage at 10 mA/cm² | cd/A | Efficiency ratio |
|---|---|---|---|---|
| Example 2-1 | Compound 1-1 + Compound 10-7 | 3.3 | 72.4 | 1.40 |
| Example 2-2 | Compound 1-2 + Compound 10-7 | 3.0 | 64.9 | 1.37 |
| Example 2-3 | Compound 1-3 + Compound 13-1 | 3.2 | 75.6 | 1.46 |

TABLE 2-continued

| | Compound | Driving voltage at 10 mA/cm² | cd/A | Efficiency ratio |
|---|---|---|---|---|
| Example 2-4 | Compound 1-4 + Compound 10-4 | 3.2 | 66.5 | 1.32 |
| Example 2-5 | Compound 1-5 + Compound 13-1 | 2.9 | 74.4 | 1.39 |
| Example 2-6 | Compound 1-6 + Compound 13-1 | 3.1 | 78.7 | 1.42 |
| Example 2-7 | Compound 1-7 + Compound 13-1 | 2.9 | 79.3 | 1.42 |
| Example 2-8 | Compound 1-8 + Compound 13-1 | 2.9 | 75.9 | 1.42 |
| Example 2-9 | Compound 1-9 + Compound 13-1 | 2.8 | 75.7 | 1.38 |
| Example 2-10 | Compound 1-10 + Compound 13-1 | 2.9 | 73.6 | 1.38 |
| Example 2-11 | Compound 1-11 + Compound 13-1 | 2.9 | 73.6 | 1.40 |
| Example 2-12 | Compound 1-12 + Compound 13-1 | 3.3 | 77.9 | 1.48 |
| Example 2-13 | Compound 2-1 + Compound 13-1 | 3.0 | 79.9 | 1.38 |
| Example 2-14 | Compound 2-2 + Compound 13-1 | 2.9 | 78.7 | 1.37 |
| Example 2-15 | Compound 3-1 + Compound 13-1 | 3.1 | 77.2 | 1.41 |
| Example 2-16 | Compound 3-2 + Compound 13-1 | 3.0 | 80.1 | 1.38 |
| Example 2-17 | Compound 4-1 + Compound 13-1 | 3.0 | 77.6 | 1.41 |
| Example 2-18 | Compound 4-2 + Compound 13-1 | 2.9 | 77.2 | 1.39 |
| Example 2-19 | Compound 4-3 + Compound 13-1 | 3.3 | 75.9 | 1.48 |
| Example 2-20 | Compound 4-4 + Compound 13-1 | 3.0 | 72.8 | 1.34 |
| Example 2-21 | Compound 4-5 + Compound 13-1 | 3.3 | 76.5 | 1.48 |
| Example 2-22 | Compound 5-1 + Compound 13-1 | 2.8 | 76.8 | 1.37 |
| Example 2-23 | Compound 6-1 + Compound 13-1 | 2.9 | 67.2 | 1.42 |
| Example 2-24 | Compound 7-1 + Compound 13-1 | 2.8 | 76.2 | 1.37 |
| Example 2-25 | Compound 8-1 + Compound 13-1 | 2.8 | 75.6 | 1.38 |
| Example 2-26 | Compound 9-1 + Compound 13-1 | 2.8 | 75.7 | 1.38 |
| Example 2-27 | Compound 9-2 + Compound 13-1 | 2.8 | 75.6 | 1.38 |
| Example 2-28 | Compound 1-1 + Compound 10-1 | 3.3 | 76.2 | 1.47 |
| Example 2-29 | Compound 1-1 + Compound 10-2 | 3.0 | 75.9 | 1.43 |
| Example 2-30 | Compound 1-1 + Compound 10-3 | 3.0 | 75.7 | 1.45 |
| Example 2-31 | Compound 1-1 + Compound 10-4 | 3.1 | 75.9 | 1.46 |
| Example 2-32 | Compound 1-1 + Compound 10-5 | 3.1 | 76.5 | 1.43 |
| Example 2-33 | Compound 1-1 + Compound 10-6 | 2.9 | 72.7 | 1.40 |
| Example 2-34 | Compound 1-1 + Compound 11-1 | 3.2 | 77.4 | 1.48 |
| Example 2-35 | Compound 1-1 + Compound 11-2 | 2.8 | 79.7 | 1.34 |
| Example 2-36 | Compound 1-1 + Compound 11-3 | 3.0 | 76.5 | 1.36 |
| Example 2-37 | Compound 1-1 + Compound 11-4 | 2.9 | 78.1 | 1.37 |
| Example 2-38 | Compound 1-1 + Compound 11-5 | 3.0 | 79.7 | 1.36 |
| Example 2-39 | Compound 1-1 + Compound 12-1 | 2.8 | 76.2 | 1.37 |
| Example 2-40 | Compound 1-1 + Compound 13-1 | 3.1 | 73.9 | 1.48 |
| Example 2-41 | Compound 1-2 + Compound 13-1 | 3.0 | 62.5 | 1.50 |
| Example 2-42 | Compound 1-4 + Compound 13-1 | 3.1 | 68.7 | 1.35 |

TABLE 3

| | Compound | Driving voltage at 10 mA/cm² | cd/A | Efficiency ratio |
|---|---|---|---|---|
| Comparative Example 2-1 | Compound 1-1 | 6.0 | 33.6 | 1.80 |
| Comparative Example 2-2 | Compound 1-2 | 4.5 | 52.1 | 1.91 |
| Comparative Example 2-3 | Compound 1-3 | 9.8 | 51.2 | 1.80 |
| Comparative Example 2-4 | Compound 1-4 | 4.3 | 56.0 | 2.17 |
| Comparative Example 2-5 | Compound 1-5 | 4.3 | 53.7 | 2.14 |
| Comparative Example 2-6 | Compound 1-6 | 3.9 | 48.7 | 2.11 |
| Comparative Example 2-7 | Compound 1-7 | 7.3 | 59.9 | 2.43 |
| Comparative Example 2-8 | Compound 1-8 | 6.1 | 44.6 | 1.68 |
| Comparative Example 2-9 | Compound 1-9 | 3.8 | 45.5 | 1.86 |
| Comparative Example 2-10 | Compound 1-10 | 3.8 | 40.6 | 1.70 |
| Comparative Example 2-11 | Compound 1-11 | 4.3 | 46.9 | 1.71 |
| Comparative Example 2-12 | Compound 1-12 | 4.4 | 47.7 | 1.71 |
| Comparative Example 2-13 | Compound 2-1 | 4.4 | 47.3 | 1.71 |
| Comparative Example 2-14 | Compound 2-2 | 4.4 | 48.0 | 1.70 |
| Comparative Example 2-15 | Compound 3-1 | 4.5 | 46.8 | 1.83 |
| Comparative Example 2-16 | Compound 3-2 | 4.5 | 50.0 | 1.69 |
| Comparative Example 2-17 | Compound 4-1 | 4.6 | 50.0 | 1.69 |
| Comparative Example 2-18 | Compound 4-2 | 4.6 | 49.5 | 1.67 |
| Comparative Example 2-19 | Compound 4-3 | 4.3 | 48.0 | 1.70 |
| Comparative Example 2-20 | Compound 4-4 | 4.5 | 45.1 | 1.85 |
| Comparative Example 2-21 | Compound 4-5 | 4.6 | 47.8 | 1.78 |
| Comparative Example 2-22 | Compound 5-1 | 4.6 | 48.2 | 1.78 |
| Comparative Example 2-23 | Compound 6-1 | 4.3 | 48.0 | 1.69 |
| Comparative Example 2-24 | Compound 7-1 | 4.7 | 51.2 | 1.68 |
| Comparative Example 2-25 | Compound 8-1 | 4.4 | 47.9 | 1.69 |
| Comparative Example 2-26 | Compound 9-1 | 4.5 | 46.7 | 1.85 |
| Comparative Example 2-27 | Compound 9-2 | 4.6 | 50.4 | 1.76 |
| Comparative Example 2-28 | Compound 10-1 | 3.8 | 66.0 | 1.96 |
| Comparative Example 2-29 | Compound 10-2 | 3.7 | 43.6 | 2.55 |

TABLE 3-continued

| | Compound | Driving voltage at 10 mA/cm² | cd/A | Efficiency ratio |
|---|---|---|---|---|
| Comparative Example 2-30 | Compound 10-3 | 4.0 | 67.1 | 1.93 |
| Comparative Example 2-31 | Compound 10-4 | 4.1 | 65.4 | 2.02 |
| Comparative Example 2-32 | Compound 10-5 | 3.1 | 35.0 | 2.02 |
| Comparative Example 2-33 | Compound 10-6 | 3.3 | 23.4 | 1.95 |
| Comparative Example 2-34 | Compound 10-7 | 4.3 | 53.7 | 2.14 |
| Comparative Example 2-35 | Compound 11-1 | 3.9 | 48.7 | 2.11 |
| Comparative Example 2-36 | Compound 11-2 | 3.7 | 60.5 | 2.02 |
| Comparative Example 2-37 | Compound 11-3 | 3.3 | 42.8 | 2.12 |
| Comparative Example 2-38 | Compound 11-4 | 3.5 | 43.1 | 2.14 |
| Comparative Example 2-39 | Compound 11-5 | 3.3 | 53.8 | 2.27 |
| Comparative Example 2-40 | Compound 12-1 | 3.4 | 21.6 | 2.37 |
| Comparative Example 2-41 | Compound 13-1 | 3.5 | 27.9 | 2.25 |
| Comparative Example 2-42 | Compound 13-2 | 6.7 | 61.0 | 1.96 |
| Comparative Example 2-43 | Comparative Example Compound A | 6.8 | 42.1 | 1.85 |
| Comparative Example 2-44 | Comparative Example Compound B | 3.7 | 50.03 | 1.70 |
| Comparative Example 2-45 | Comparative Example Compound A + Comparative Example Compound B | 5.2 | 52.7 | 1.94 |

TABLE 4

| | Compound | Cd/A (at max) | Cd/A (10 mA/cm²) | Cd/A (at 100 mA/cm²) | Efficiency ratio Cd/A (at max)/Cd/A (at 100 mA/cm²) |
|---|---|---|---|---|---|
| Comparative Example 2-2 | Compound 1-2 | 55.8 | 52.1 | 29.2 | 1.91 |
| Comparative Example 2-16 | Compound 3-2 | 55.8 | 50.0 | 32.9 | 1.39 |
| Comparative Example 2-34 | Compound 10-7 | 61.6 | 53.7 | 28.8 | 2.14 |
| Comparative Example 2-41 | Compound 13-1 | 29.5 | 27.9 | 13.1 | 2.25 |
| Comparative Example 2-43 | Comparative Example Compound A | 51.8 | 42.1 | 28.1 | 1.85 |
| Comparative Example 2-44 | Comparative Example Compound B | 58.8 | 50.03 | 34.6 | 1.70 |
| Comparative Example 2-45 | Comparative Example Compound A + Comparative Example Compound B | 69.1 | 52.7 | 35.6 | 1.94 |
| Example 2-2 | Compound 1-2 + Compound 10-7 | 69.3 | 64.9 | 50.5 | 1.37 |
| Example 2-16 | Compound 3-2 + Compound 13-1 | 88.6 | 80.1 | 64.2 | 1.38 |

EXPLANATION OF REFERENCE NUMERALS AND SYMBOLS

1: Substrate
2: Anode
3: Light emitting layer
4: Cathode

The invention claimed is:
1. An organic light emitting device comprising:
an anode;
a cathode disposed to face the anode; and
a light emitting layer disposed between the anode and the cathode,
wherein the light emitting layer comprises: a host comprising a P-type host and an N-type host, which produce an exciplex; and a phosphorescent dopant,
wherein the host comprising the P-type host and the N-type host, which produce an exciplex, emits a photoluminescence light with a longer wavelength than a wavelength of each of the P-type host and the N-type host,
wherein the P-type host is any one or more selected from compounds represented by the following Chemical Formulae 1 to 9, and the N-type host is any one or more selected from compounds represented by the following Chemical Formula 11:

[Chemical Formula 1]
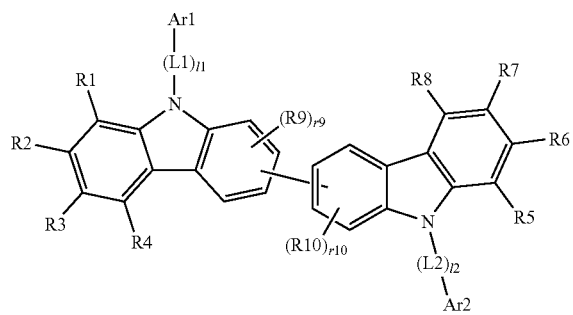
[Chemical Formula 2]
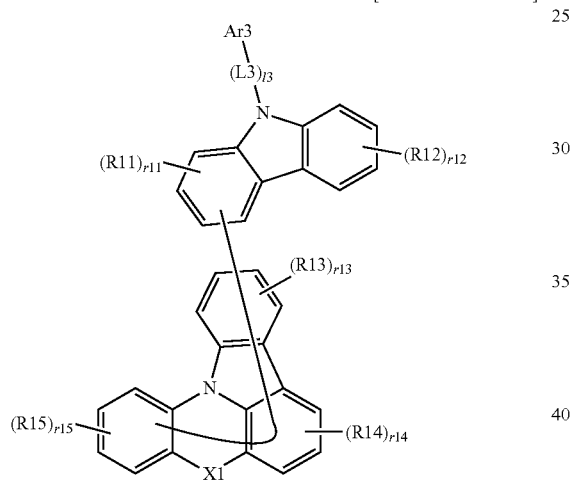
[Chemical Formula 3]
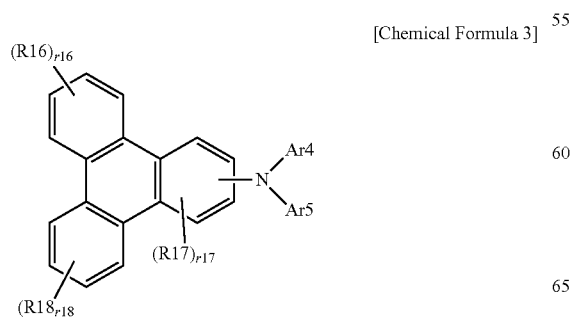
[Chemical Formula 4]
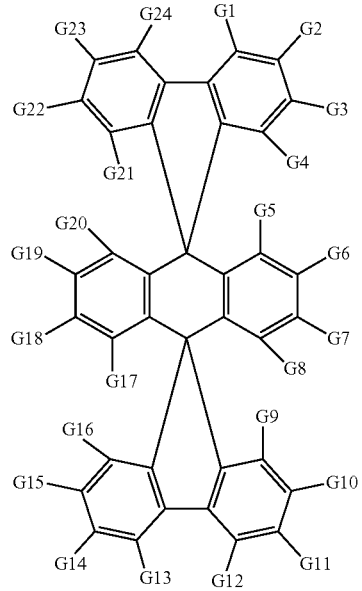
[Chemical Formula 5]
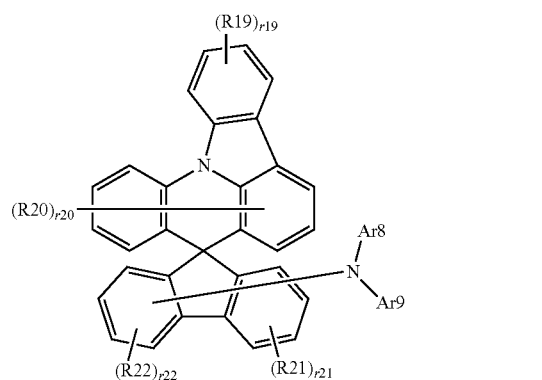
[Chemical Formula 6]
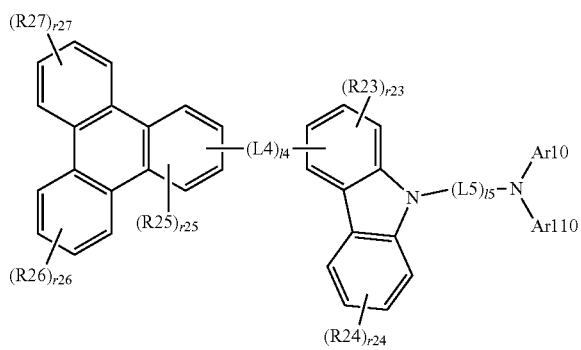

-continued

[Chemical Formula 7]

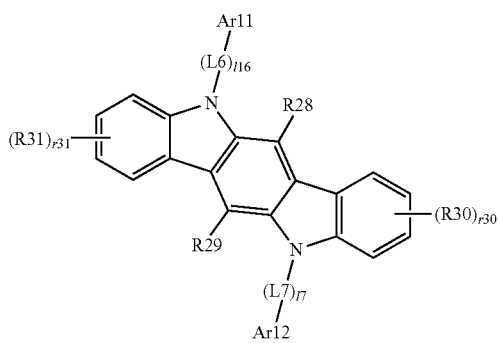

[Chemical Formula 8]

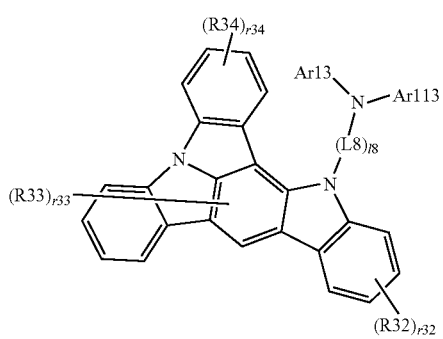

[Chemical Formula 9]

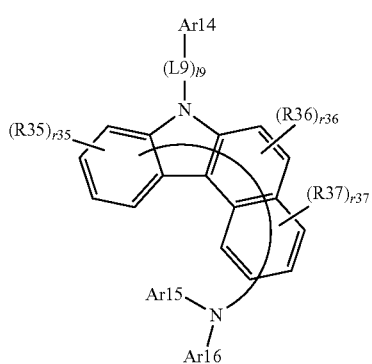

in Chemical Formulae 1 to 9,
X1 is O or S,
at least one of G1 to G24 is

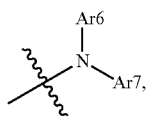

and the others are hydrogen,
L1 to L9 are the same as or different from each other, and are each independently a direct bond; or a substituted or unsubstituted arylene group,
Ar1 to Ar16, Ar110, and Ar113 are the same as or different from each other, and are each independently a substituted or unsubstituted aryl group,
R1 to R37 are the same as or different from each other, and are each independently hydrogen; a substituted or unsubstituted alkyl group; or a substituted or unsubstituted aryl group; or a substituted or unsubstituted carbazolyl group, or adjacent groups are optionally bonded to each other to form a substituted or unsubstituted ring,
l1 to l9 are each 1 or 2,
when l1 to l9 are each a plural number, a plurality of structures in the parenthesis are the same as or different from each other,
r36 is 1 or 2,
r9, r10, r11, r14, r17, r23, and r25 are each 1 to 3,
r12, r13, r15, r16, r18, r19, r21, r22, r24, r26, r27, r30, 131, r32, r34, 135, and r37 are each 1 to 4,
r33 is 1 to 5,
r20 is 1 to 7,
$3 \le r13+r14+r15 \le 10$,
$2 \le r21+r22 \le 7$,
$3 \le r35+r36+r37 \le 9$, and
when l9 to r27 and r30 to 137 are each a plural number, a plurality of structures in the parenthesis are the same as or different from each other,

[Chemical Formula 11]

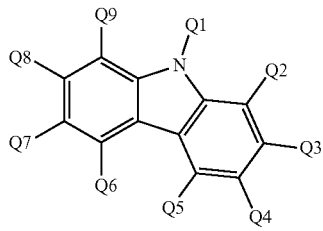

in Chemical Formula 11,
at least one of Q1 to Q9 is

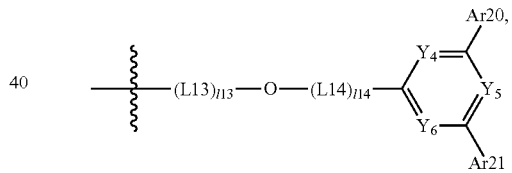

and the others are hydrogen; a substituted or unsubstituted aryl group; or a substituted or unsubstituted heteroaryl group,
at least one of Y4 to Y6 is N, and the others are CH,
L13 and L14 are the same as or different from each other, and are each independently a direct bond; or a substituted or unsubstituted arylene group,
Ar20 and Ar21 are the same as or different from each other, and are each independently a substituted or unsubstituted aryl group,
l13 and l14 are each 1 or 2, and
when l13 and l14 are each a plural number, a plurality of structures in the parenthesis are the same as or different from each other.

2. The organic light emitting device of claim 1, wherein a photoluminescence peak of the host comprising the P-type host and the N-type host, which produce an exciplex, has lower photon energy than a photon energy of each photoluminescence peak of the P-type host and the N-type host.

3. The organic light emitting device of claim 1, wherein a HOMO energy level of the P-type host is higher than a HOMO energy level of the N-type host.

4. The organic light emitting device of claim 1, wherein a LUMO energy level of the N-type host is lower than a LUMO energy level of the P-type host.

5. The organic light emitting device of claim 1, wherein the host comprises the P-type host: the N-type host at a weight ratio of 2:8 to 8:2.

6. The organic light emitting device of claim 1, wherein an efficiency ratio of the organic light emitting device according to a change in current density is 1.6 or less.

7. The organic light emitting device of claim 1, wherein the P-type host is selected from the following compounds:

1-1

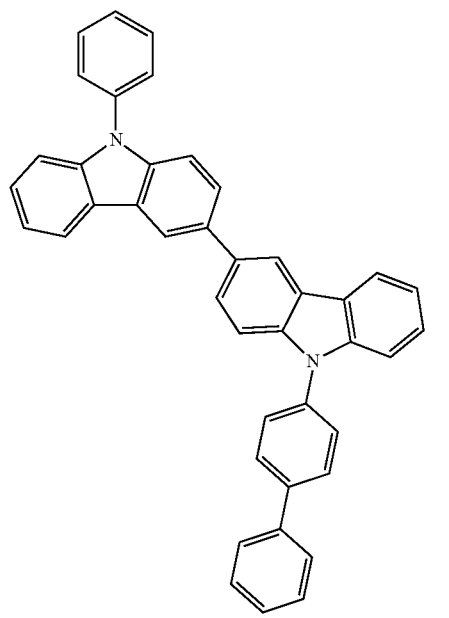

1-2

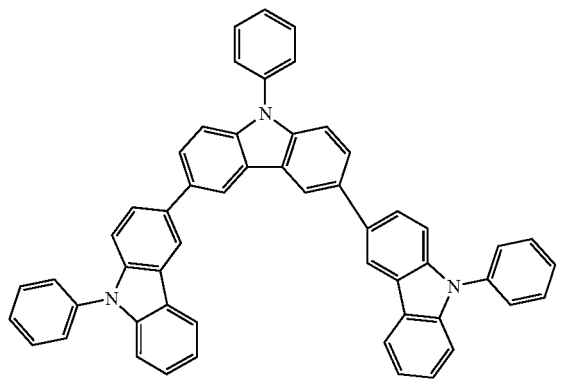

1-3

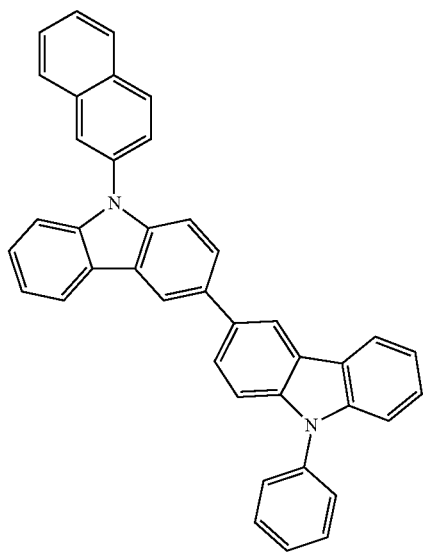

1-4

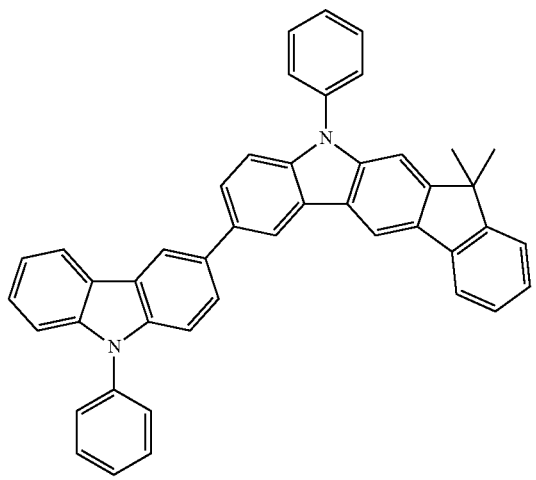

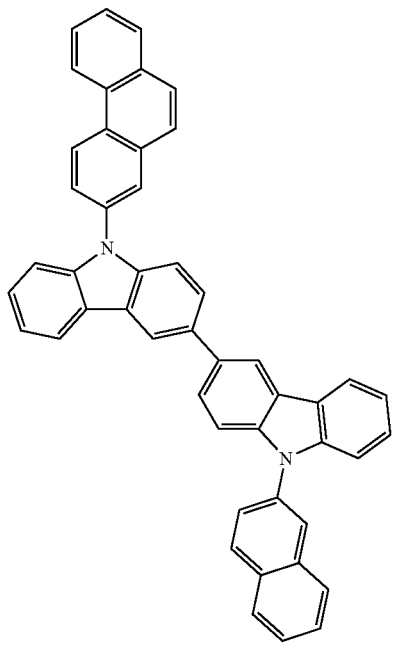
1-5
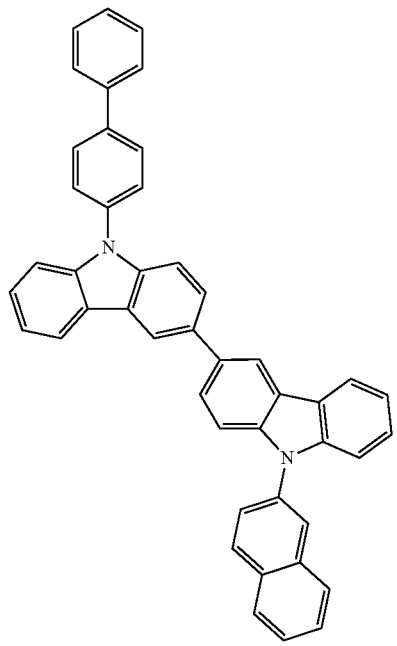
1-7
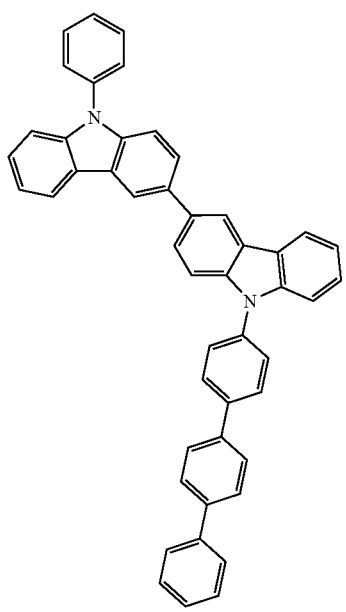
1-6
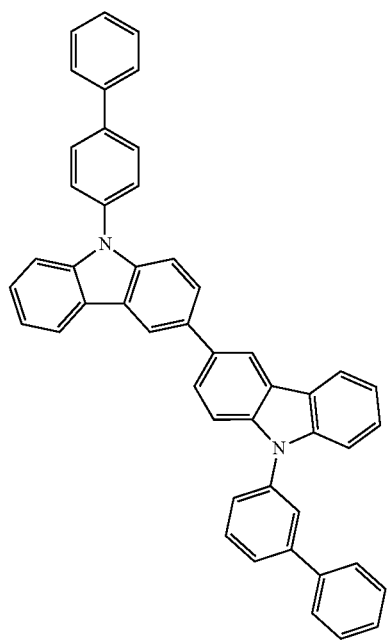
1-8

1-9
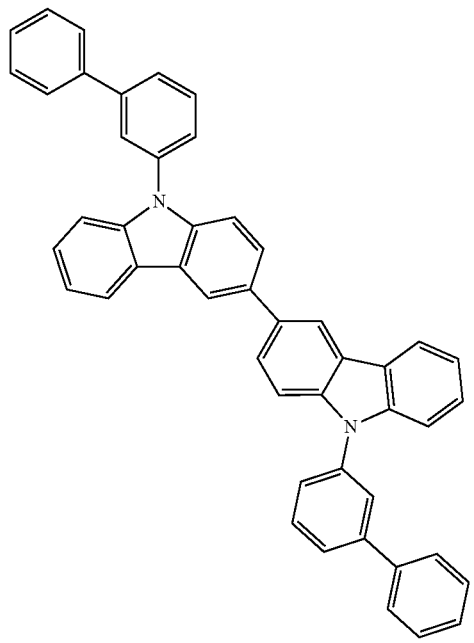
1-11
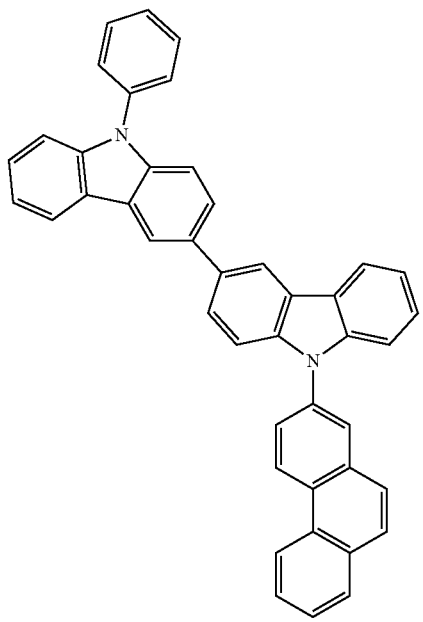
1-10
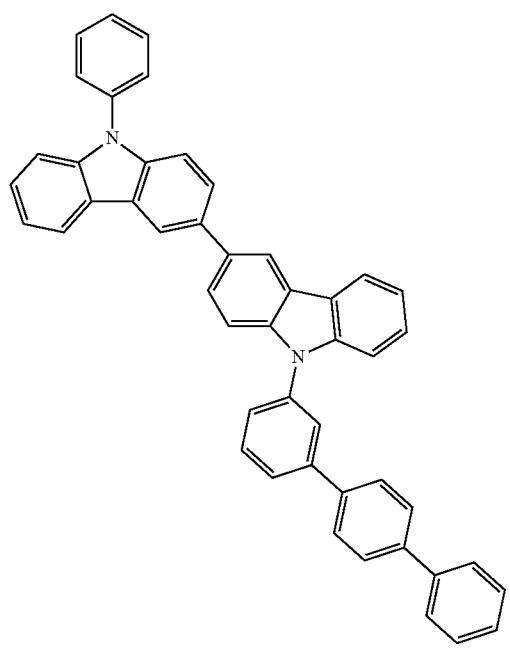
1-12
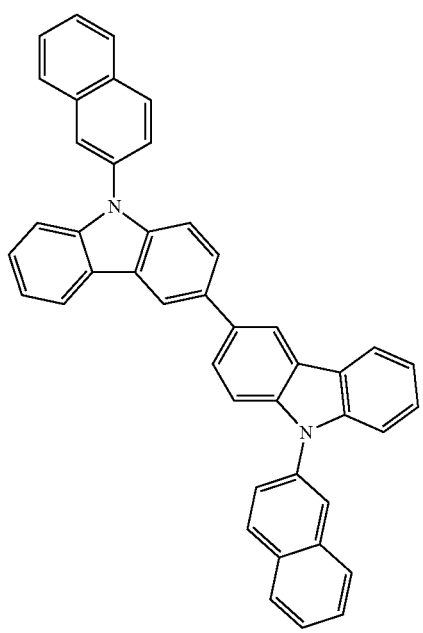

1-13
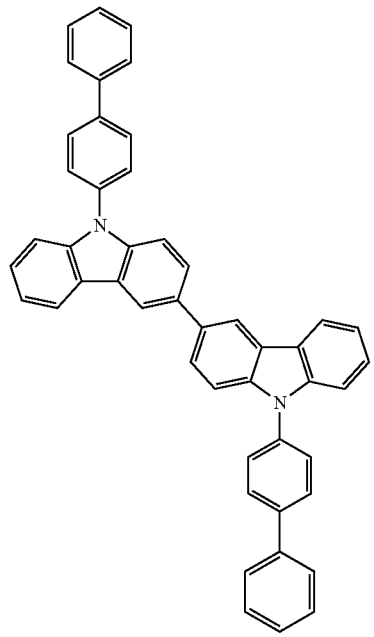
1-14
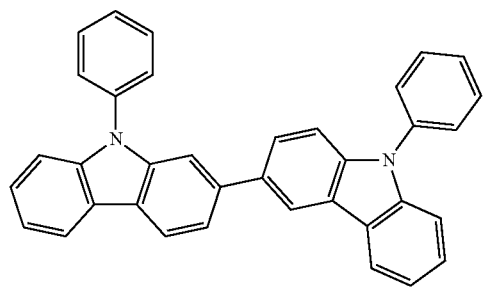
1-15
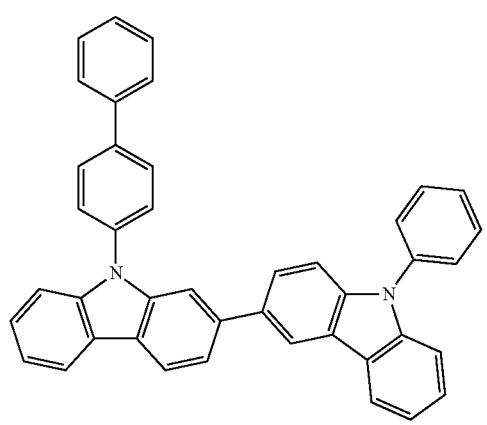
1-16
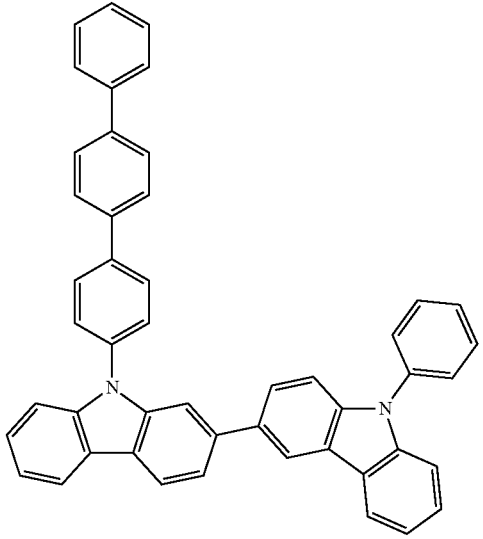
1-17
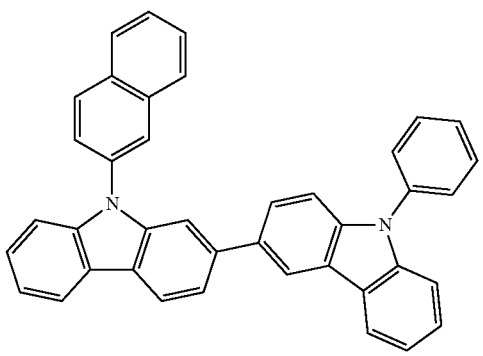
1-18
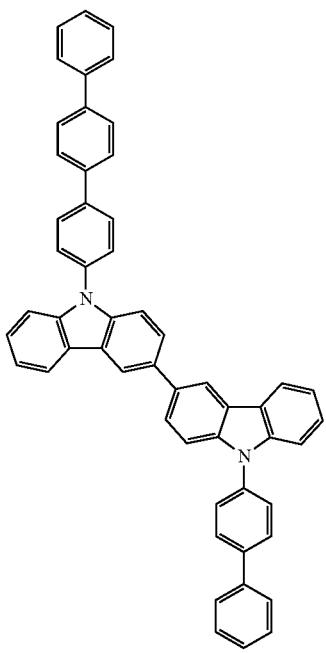

-continued
1-19
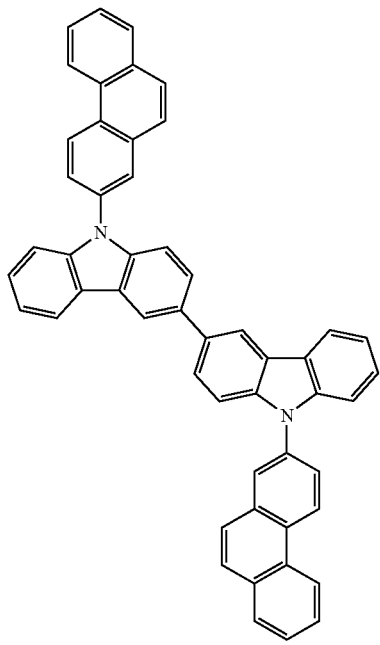
1-20
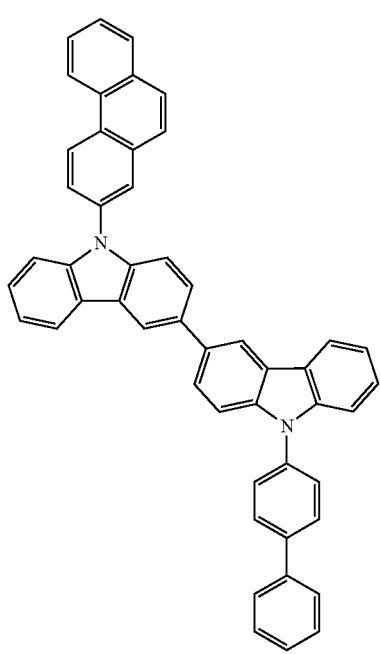
1-21
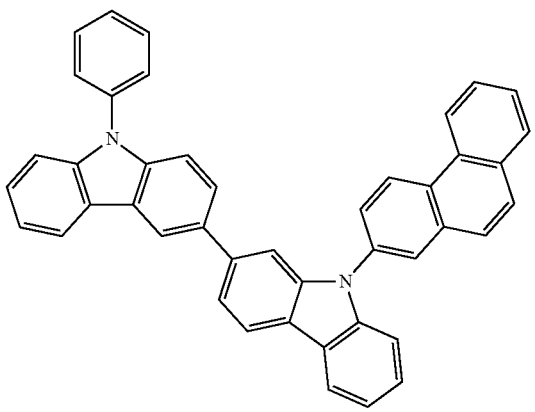
1-22
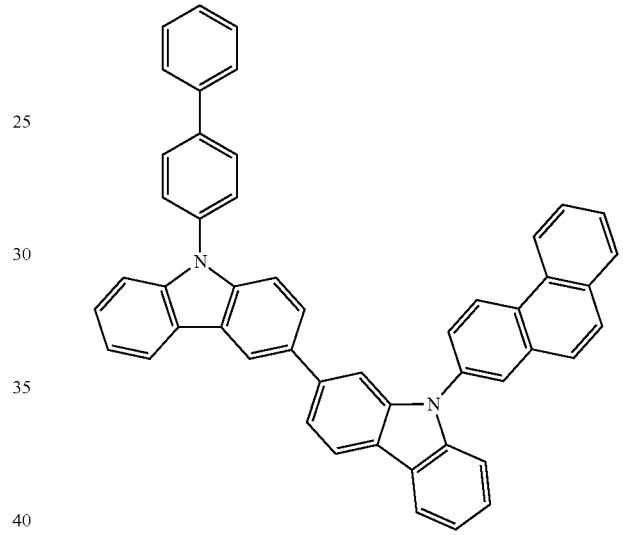
1-23
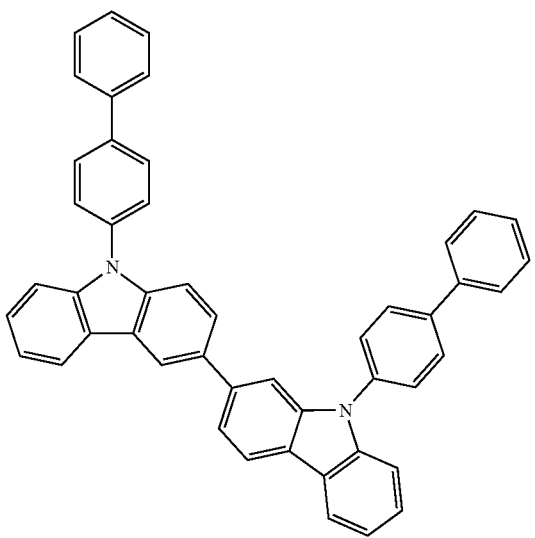

1-24
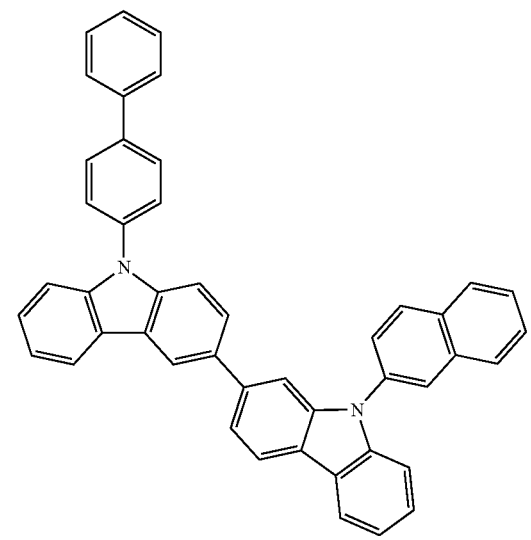
1-25
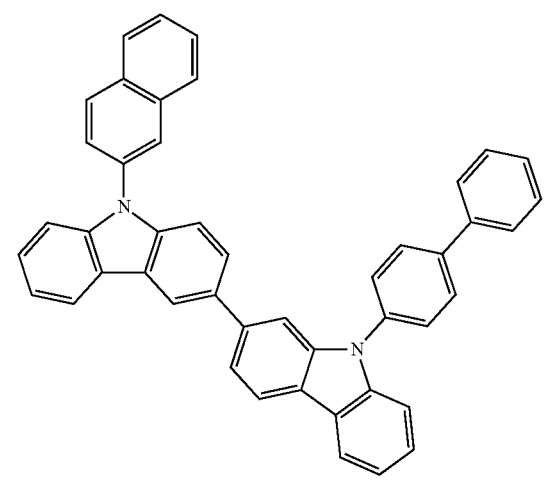
1-26
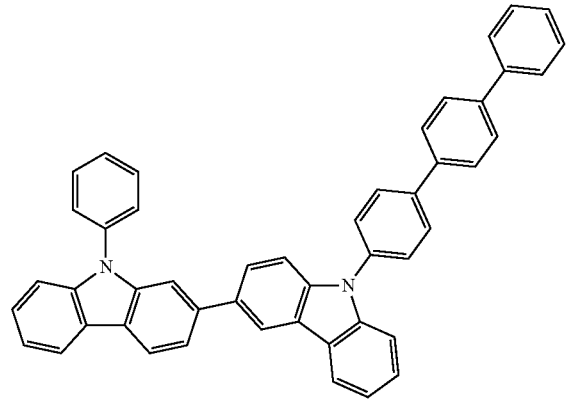
1-27
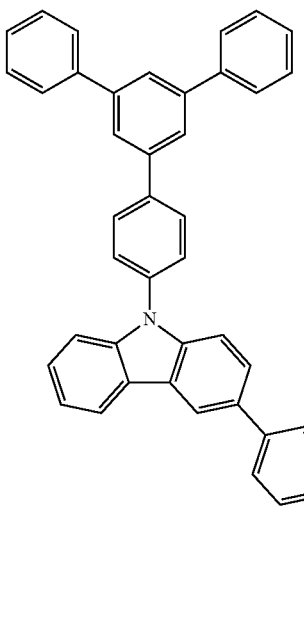
2-1
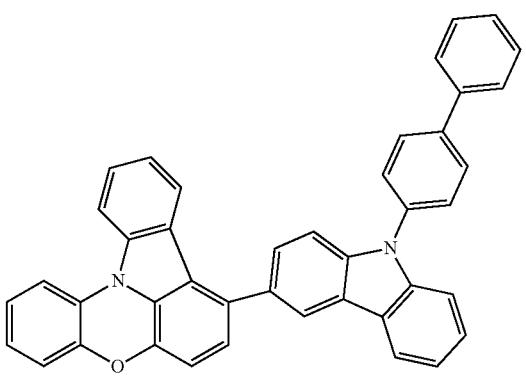
2-2
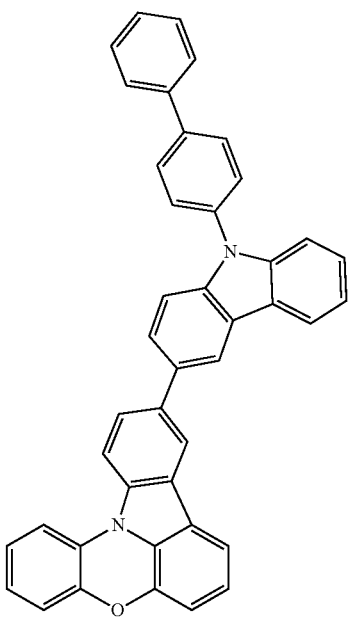

3-1
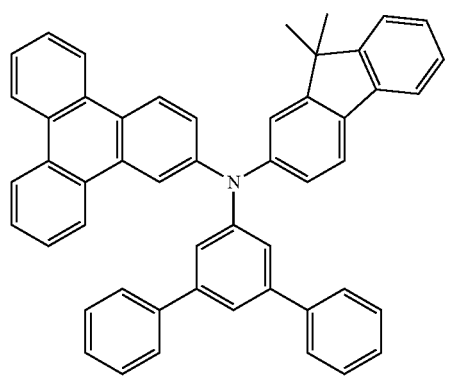
3-2
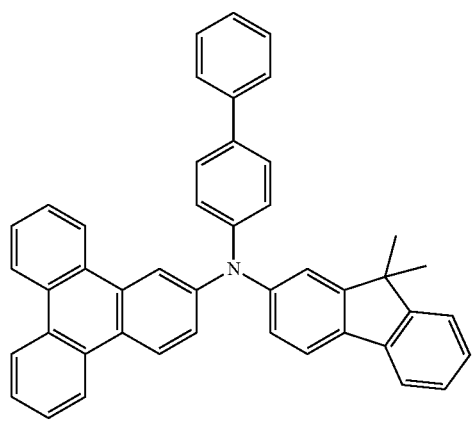
3-3
4-1
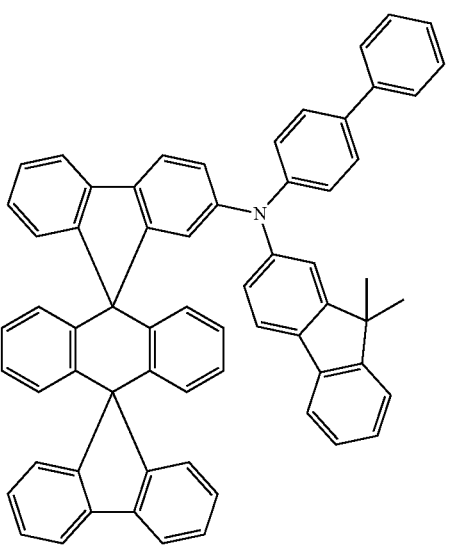
4-2
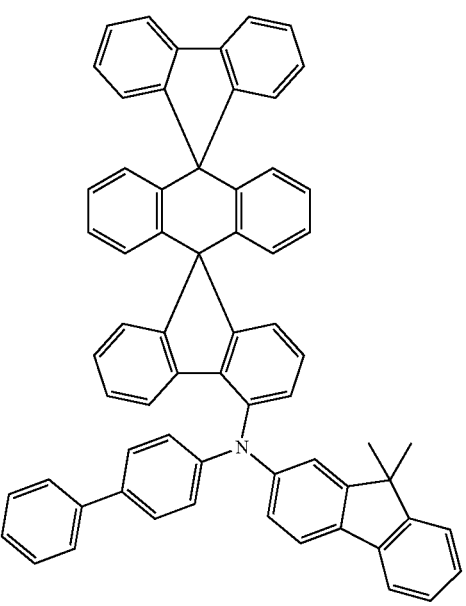

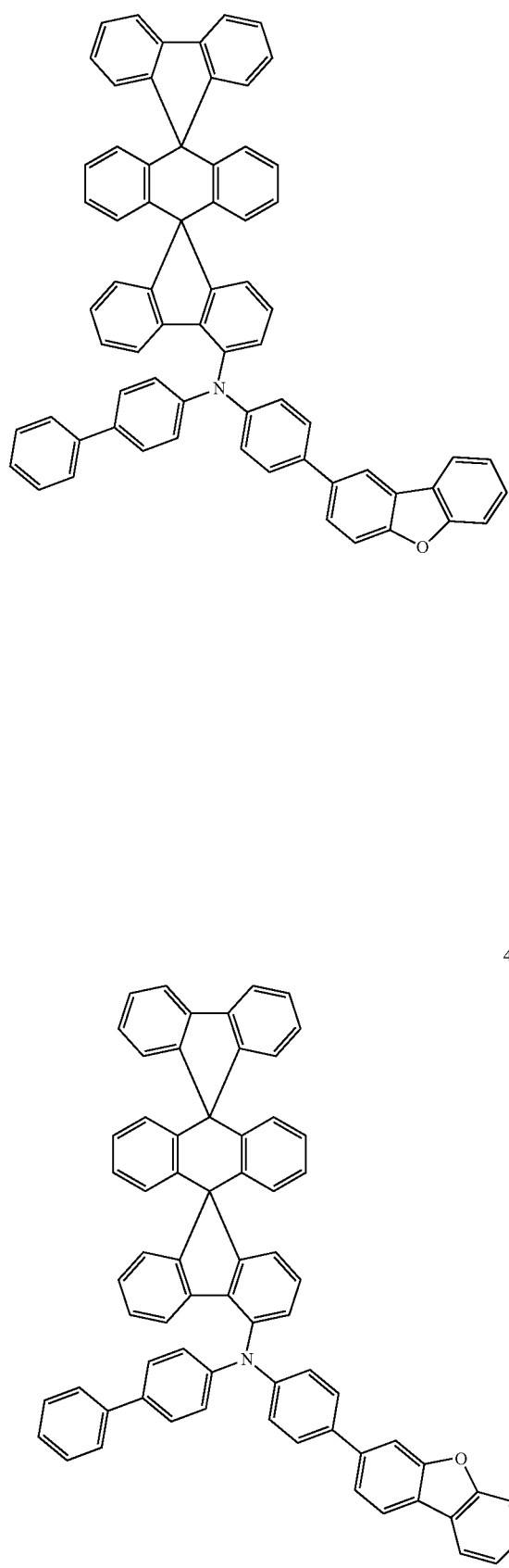
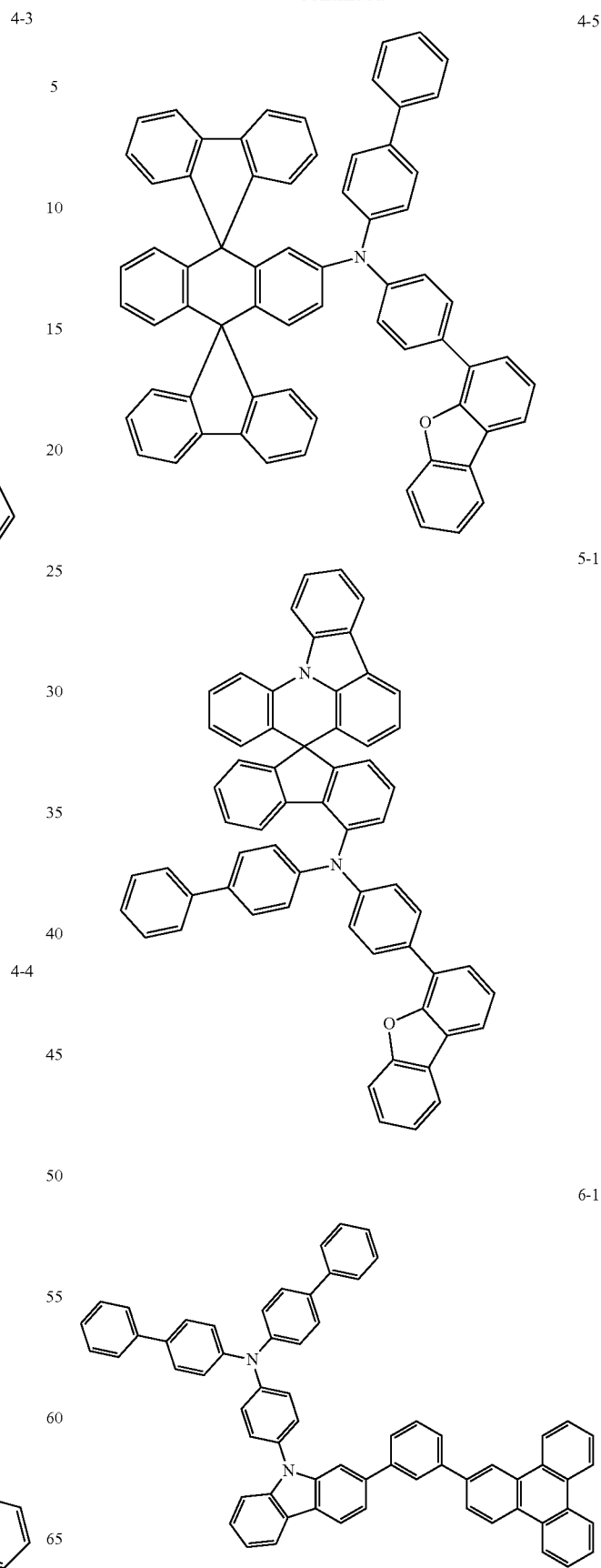

7-1
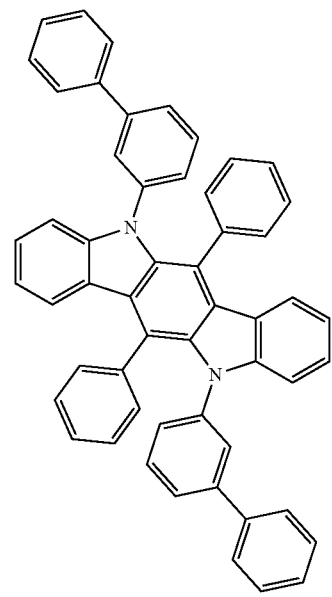
8-1
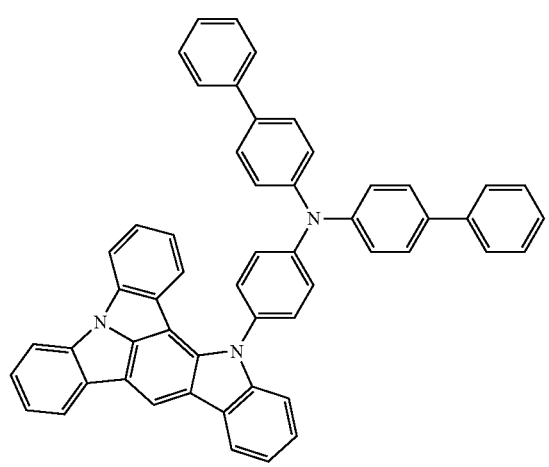
9-1
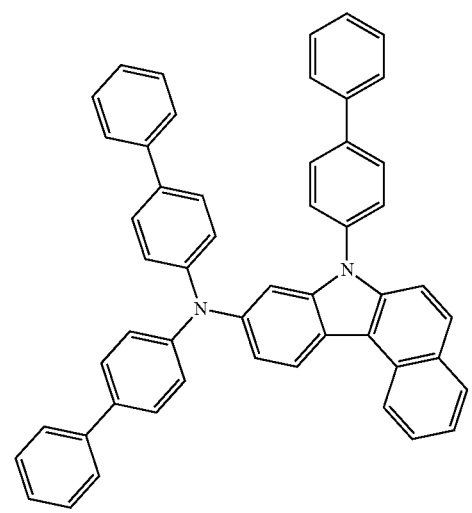
9-2
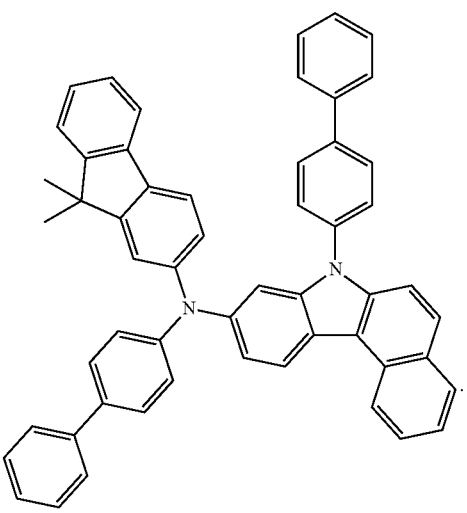
8. The organic light emitting device of claim 1, wherein the N-type host is selected from the following compounds:
11-1
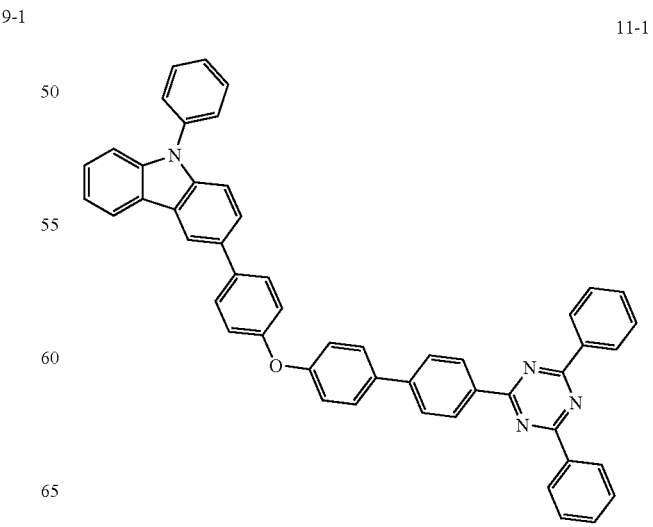

11-2
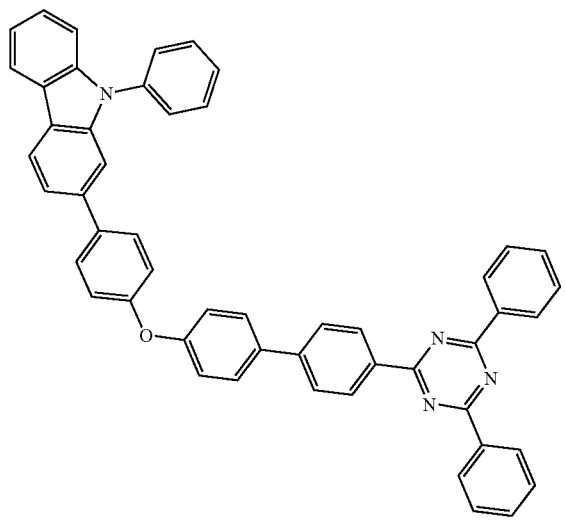
11-3
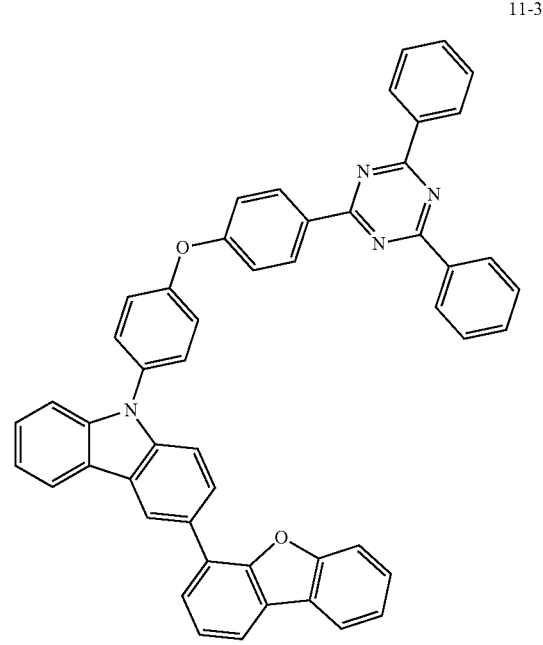
11-4
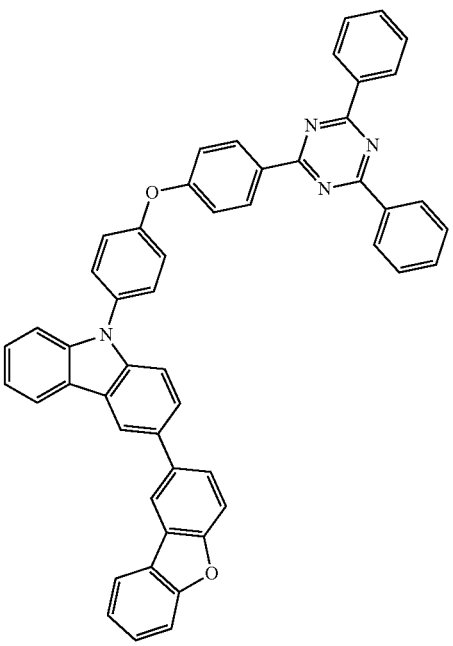
11-5
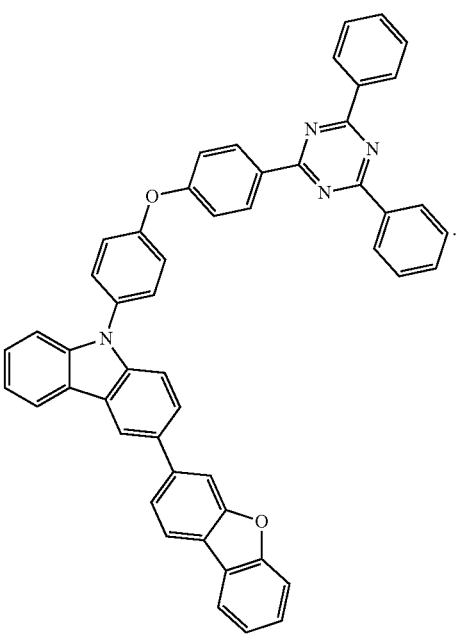
* * * * *